US012622903B2

(12) United States Patent
Plucinski et al.

(10) Patent No.: US 12,622,903 B2
(45) **Date of Patent: *May 12, 2026**

(54) DRUG PRODUCTS FOR INTRANASAL ADMINISTRATION AND USES THEREOF

(71) Applicant: Summit Biosciences Inc., Lexington, KY (US)

(72) Inventors: Gregory G. Plucinski, Nicholasville, KY (US); Adrian T. Raiche, Lexington, KY (US); Kristi R. Sims, Versailles, KY (US)

(73) Assignee: SUMMIT BIOSCIENCES INC., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,972

(22) Filed: Mar. 12, 2024

(65) Prior Publication Data

US 2024/0226093 A1 Jul. 11, 2024

Related U.S. Application Data

(63) Continuation of application No. 17/882,014, filed on Aug. 5, 2022, now abandoned, which is a continuation of application No. PCT/US2021/016873, filed on Feb. 5, 2021.

(60) Provisional application No. 62/970,629, filed on Feb. 5, 2020.

(51) Int. Cl.

| | |
|---|---|
| ***A61K 31/485*** | (2006.01) |
| ***A61K 9/00*** | (2006.01) |
| ***A61K 9/08*** | (2006.01) |
| ***A61K 47/10*** | (2017.01) |
| ***A61K 47/12*** | (2006.01) |

(52) U.S. Cl.

CPC .......... *A61K 31/485* (2013.01); *A61K 9/0043* (2013.01); *A61K 9/08* (2013.01); *A61K 47/10* (2013.01); *A61K 47/12* (2013.01)

(58) Field of Classification Search

CPC ...... A61K 31/485; A61K 9/0043; A61K 9/08; A61K 47/10; A61K 47/12; A61P 25/36; A61M 11/007; A61M 15/08; A61M 2209/06

See application file for complete search history.

(56) References Cited

U.S. PATENT DOCUMENTS

| | | | |
|---|---|---|---|
| 4,983,595 | A | 1/1991 | Benjamin et al. |
| 6,525,062 | B2 | 2/2003 | Levine |
| 6,713,470 | B2 | 3/2004 | Jackson et al. |
| 8,124,126 | B2 | 2/2012 | Bosse et al. |
| 8,470,361 | B2 | 6/2013 | Pettersson |
| 9,192,570 | B2 | 11/2015 | Wyse et al. |
| 9,211,253 | B2 | 12/2015 | Crystal et al. |
| 9,211,293 | B2 | 12/2015 | Deaver et al. |
| 9,289,425 | B2 | 3/2016 | Wyse et al. |
| 9,468,747 | B2 | 10/2016 | Crystal et al. |
| 9,480,644 | B2 | 11/2016 | Crystal et al. |
| 9,561,177 | B2 | 2/2017 | Keegan et al. |
| 9,629,965 | B2 | 4/2017 | Crystal et al. |
| 9,642,848 | B2 | 5/2017 | Amancha et al. |
| 9,707,226 | B2 | 7/2017 | Keegan et al. |
| 9,775,838 | B2 | 10/2017 | Keegan et al. |
| 10,085,937 | B2 | 10/2018 | Keegan et al. |
| 10,143,792 | B2 | 12/2018 | Edwards et al. |
| 10,188,632 | B2 | 1/2019 | Costello et al. |
| 10,722,510 | B2 | 7/2020 | Amancha et al. |

(Continued)

FOREIGN PATENT DOCUMENTS

| | | | |
|---|---|---|---|
| CA | 3078941 | A1 | 4/2019 |
| CN | 1575795 | A | 2/2005 |

(Continued)

OTHER PUBLICATIONS

"The Protein Man". G-Biosciences [online]; 2014; downloaded from <URL https://info.gbiosciences.com/blog/bid/197554/biological-buffers-ph-range-and-how-to-prepare-them > on May 31, 2024; 3 pages. (Year: 2014).*

Beasley, et al. "Preservatives in nebulizer solutions: risks without benefit. Pharmacotherapy." Jan.-Feb. 1998;18(1):130-9. PMID: 9469687.

International Search Report and Written Opinion mailed Oct. 31, 2019 for International Application No. PCT/US2019/045300 filed Aug. 6, 2019. (13 pages).

International Search Report and Written Opinion mailed Oct. 31, 2019 for International Application No. PCT/US2021/016873 filed Feb. 5, 2021. (13 pages).

(Continued)

*Primary Examiner* — David Browe

(74) *Attorney, Agent, or Firm* — STERNE, KESSLER, GOLDSTEIN & FOX P.L.L.C.; Cynthia DeRenzo

(57) ABSTRACT

Provided herein are drug products adapted for nasal delivery comprising a device and a pharmaceutical composition comprising an opioid receptor antagonist, wherein the claimed invention provides a unit dose of an aqueous pharmaceutical solution, or aqueous pharmaceutical composition, housed in a device configured for intranasal administration to a patient, wherein the aqueous pharmaceutical solution consists of, or the aqueous pharmaceutical composition consists essentially of: (i) naloxone hydrochloride in an amount of about 9% by weight based on the total weight of the aqueous pharmaceutical solution; (ii) glycerin in an amount of about 1.4% by weight based on the total weight of the aqueous pharmaceutical solution; (iii) a citrate buffer system adjusted by hydrochloric acid and/or sodium hydroxide; and (iv) United States Pharmacopeia (USP)-grade Purified Water; wherein the pH of the aqueous pharmaceutical solution is from about 3.5 to about 4.7; and wherein the hydrochloric acid and the sodium hydroxide may each be independently present in the aqueous pharmaceutical solution, as required, to achieve the pH from about 3.5 to about 4.7.

7 Claims, 10 Drawing Sheets

(56) References Cited

U.S. PATENT DOCUMENTS

| | | | | |
|---|---|---|---|---|
| 10,973,814 | B2 | 4/2021 | Amancha et al. | |
| 2003/0004178 | A1 | 1/2003 | Chapleo et al. | |
| 2004/0180916 | A1 | 9/2004 | Levine | |
| 2005/0101621 | A1 | 5/2005 | Lipsky | |
| 2007/0261695 | A1* | 11/2007 | Kottayil | A61P 25/20 604/407 |
| 2010/0010031 | A1 | 1/2010 | Yum, II et al. | |
| 2011/0021583 | A1* | 1/2011 | Holl | A61K 9/006 514/415 |
| 2012/0270895 | A1 | 10/2012 | Wermeling | |
| 2013/0122077 | A1 | 5/2013 | Al-Ghananeem | |
| 2015/0174061 | A1 | 6/2015 | Wyse et al. | |
| 2015/0258019 | A1 | 9/2015 | Crystal et al. | |
| 2016/0008349 | A1* | 1/2016 | Amancha | A61P 25/36 514/282 |
| 2016/0136157 | A1 | 5/2016 | Wyse et al. | |
| 2016/0296516 | A1 | 10/2016 | Danagher et al. | |
| 2016/0324849 | A1 | 11/2016 | Finn et al. | |
| 2016/0354363 | A1 | 12/2016 | Amancha et al. | |
| 2017/0071851 | A1 | 3/2017 | Keegan et al. | |
| 2017/0151230 | A1 | 6/2017 | Keegan et al. | |
| 2017/0151260 | A1 | 6/2017 | Hariharan | |
| 2017/0182031 | A1 | 6/2017 | Reiz et al. | |
| 2017/0209431 | A1 | 7/2017 | Myers et al. | |
| 2017/0231904 | A1 | 8/2017 | Strang et al. | |
| 2017/0252337 | A1 | 9/2017 | Amancha et al. | |
| 2017/0258911 | A1 | 9/2017 | Sanghvi et al. | |
| 2017/0304192 | A1 | 10/2017 | Strang et al. | |
| 2017/0304295 | A1 | 10/2017 | Crystal et al. | |
| 2017/0342084 | A1 | 11/2017 | Mccarthy et al. | |
| 2018/0008595 | A1 | 1/2018 | Oksche et al. | |
| 2018/0147143 | A1 | 5/2018 | Amancha et al. | |
| 2018/0153812 | A1 | 6/2018 | Mannion et al. | |
| 2018/0169006 | A1 | 6/2018 | Crystal et al. | |
| 2018/0313858 | A1 | 11/2018 | Liu et al. | |
| 2018/0360822 | A1 | 12/2018 | Wyse et al. | |
| 2019/0015323 | A1 | 1/2019 | Keegan et al. | |
| 2019/0269780 | A1 | 9/2019 | Lowenthal et al. | |
| 2020/0030229 | A1 | 1/2020 | Keegan et al. | |
| 2021/0186954 | A1 | 6/2021 | Plucinski et al. | |
| 2021/0401827 | A1 | 12/2021 | Crystal et al. | |
| 2022/0387421 | A1 | 12/2022 | Plucinski et al. | |
| 2024/0216360 | A1 | 7/2024 | Plucinski et al. | |

FOREIGN PATENT DOCUMENTS

| | | | |
|---|---|---|---|
| EP | 707446 | A1 | 4/1996 |
| EP | 1534254 | A2 | 6/2005 |
| EP | 2001445 | B1 | 7/2014 |
| EP | 2915525 | A1 | 9/2015 |
| EP | 2787978 | B1 | 9/2016 |
| EP | 2568967 | B1 | 10/2018 |
| WO | 2015/136373 | A1 | 9/2015 |
| WO | 2016/146981 | A1 | 9/2016 |
| WO | 2017/049181 | A1 | 3/2017 |
| WO | 2017/223566 | A1 | 12/2017 |
| WO | 2018/025089 | A2 | 2/2018 |
| WO | 2018/034920 | A1 | 2/2018 |
| WO | 2018/064672 | A1 | 4/2018 |
| WO | 2018/132725 | A1 | 7/2018 |
| WO | 2018224674 | A1 | 12/2018 |

OTHER PUBLICATIONS

Laborde-Castérot, et al.. "Occupational rhinitis and asthma due to EDTA-containing detergents or disinfectants." Am J Ind Med. Aug. 2012;55(8):677-82. doi: 10.1002/ajim.22036. Epub Mar. 16, 2012. PMID: 22431256.

The Protein Man (I.e. Anonymous). G-Biosciences [online]; 2014; downloaded from <URL https://info.gbiosciences.com/blog/bid/ 197554/ biological-buffers-ph-range-and-how-to-prepare-them > on Oct. 20, 2022; 3 pages. (Year: 2014).

Response to Office Action of U.S. Appl. No. 14/730,585 dated Oct. 7, 2016, 6 pages.

Saindane, et al. "Nanosuspension Based in Situ Gelling Nasal Spray of Carvedilol: Development, In Vitro and In Vivo Characterization," AAPS PharmaSciTech, vol. 14, No. 1, Mar. 2013, pp. 189-199.

Van Laar, et al. "The role of EDTA in provoking allergic reactions to subcutaneous infusion of apomorphine in patients with Parkinson's disease: a histologic study." Mov Disord. Jan. 1998;13(1):52-5. doi: 10.1002/mds.870130113. PMID: 9452326.

U.S. Appl. No. 17/168,519, filed Feb. 5, 2021, Pending, US 2021-0186954 A1.

U.S. Appl. No. 18/602,984, filed Mar. 12, 2024, Pending.

Extended European Search Report, European Application No. 21750411.7, dated Aug. 1, 2024.

KLOXXADO (naloxone hydrochloride) nasal spray, U.S. Food and Drug Administration Label and Prescribing Information, revised Aug. 2025, 17 pages.

Lemen, P.M., et al., "High-dose naloxone formulations are not as essential as we thought," Harm Reduction Journal 21:93, BioMed Central, United Kingdom (May 2024), 17 pages.

Hikma Pharmaceuticals USA Inc., "US FDA Approves KLOXXADOR (naloxone HC1) Nasal Spray 8 mg to Treat Opioid Overdose," Kloxxado.com (Oct. 2021), accessed at https://kloxxado.com/blog/us-fda-approves-kloxxado-naloxone-hel-nasal-spray-8-mg-to-treat-opioid-overdose/ on Oct. 20, 2025, 3 pages.

Patent and Exclusivity Search Results for Appl. No. N212045 (Naloxone Hydrochloride (KLOXXADO) Spray 8MG/SPRAY) from the U.S. Food and Drug Administration's "Orange Book: Approved Drug Products with Therapeutic Equivalence Evaluations," accessed at https://www.accessdata.fda.gov/scripts/cder/ob/patent_info.cfm?Product_No=001&Appl_No=212045&Appl_type=N on Oct. 20, 2025, 2 pages.

Payne, E.R., et al., "Comparison of Administration of 8-Milligram and 4-Milligram Intranasal Naloxone by Law Enforcement During Response to Suspected Opioid Overdose—New York, Mar. 2022-Aug. 2023," Morbidity and Mortality Weekly Report 73(5):110-113, Centers for Disease Control and Prevention, United States (Feb. 2024), 4 pages.

Final Rejection mailed Jul. 22, 2025, in U.S. Appl. No. 18/602,984, Plucinski, G.G., et al., filed Mar. 12, 2024, 15 pages.

Non-Final Rejection mailed Apr. 3, 2025, in U.S. Appl. No. 18/602,984, Plucinski, G.G., et al., filed Mar. 12, 2024, 17 pages.

Final Rejection mailed Sep. 12, 2024, in U.S. Appl. No. 18/602,984, Plucinski, G.G., et al., filed Mar. 12, 2024, 13 pages.

Non-Final Rejection mailed Jun. 11, 2024, in U.S. Appl. No. 18/602,984, Plucinski, G.G., et al., filed Mar. 12, 2024, 11 pages.

Non-Final Rejection mailed Sep. 13, 2023, in U.S. Appl. No. 17/882,014, Plucinski, G.G., et al., filed Aug. 5, 2022, 12 pages.

Final Rejection mailed May 15, 2023, in U.S. Appl. No. 17/882,014, Plucinski, G.G., et al., filed Aug. 5, 2022, 15 pages.

Non-Final Rejection mailed Oct. 27, 2022, in U.S. Appl. No. 17/882,014, Plucinski, G.G., et al., filed Aug. 5, 2022, 13 pages.

Clarke, S.F.J., et al., "Naloxone in opioid poisoning: walking the tightrope," Emergency Medicine Journal 22(9):612-616, BMJ Publishing Group, United Kingdom (Sep. 2005), 5 pages.

Connors, N.J., and Nelson, L.S., "The Evolution of Recommended Naloxone Dosing for Opioid Overdose by Medical Specialty," Journal of Medical Toxicology 12(3):276-281, Springer, United States (Sep. 2016), 6 pages.

Heishman, S.J., et al., "Acute Opioid Physical Dependence in Humans: Effect of Naloxone at 6 and 24 Hours Postmorphine," Pharmacology, Biochemistry, & Behavior 36(2):393-399, Pergamon Press, United States (Jun. 1990), 7 pages.

Stitzer, M.L., et al., "Time course of naloxone-precipitated withdrawal after acute methadone exposure in humans," Drug and Alcohol Dependence 29(1):39-46, Elsevier Scientific Publishers, Ireland (Dec. 1991), 8 pages.

Trøstheim, M., et al., "Opioid antagonism in humans: a primer on optimal dose and timing for central mu-opioid receptor blockade," Neuropsychopharmacology 48(2):299-307, Nature Publishing Group, United Kingdom (published online Aug. 2022), 9 pages.

Applicant-Initiated Interview Summary mailed Oct. 17, 2025, in U.S. Appl. No. 18/602,984, Plucinski, G.G., et al., Filing Date: Mar. 12, 2024, 3 pages.

(56) References Cited

OTHER PUBLICATIONS

Notice of Allowance mailed on Nov. 10, 2025, in U.S. Appl. No. 18/602,984, Plucinski, G.G., et al., Filing Date: Mar. 12, 2024, 10 pages.

* cited by examiner

| Ingredient | Amount | | | | | | | | | |
|---|---|---|---|---|---|---|---|---|---|---|
| **Naloxone HCl Dose (per 100 µL)** | 0 mg | 10 mg | 10 mg | 10 mg | 10 mg | 10 mg | 10 mg | 10 mg | 10 mg | 10 mg |
| **Naloxone HCl Dihydrate** | 0 g | 109.9 g | 10.99 g | 10.99 g | 10.99 g | 10.99 g | 10.99 g | 54.95 g | 10.99 g | 10.99 g |
| Citric Acid, Anhydrous | 90 mg | 85.7 mg | 8.57 mg | 8.57 mg | 8.57 mg | 8.57 mg | 8.57 mg | 21.4 mg | 4.29 mg | 4.29 mg |
| Trisodium Citrate Dihydrate | 150 mg | 148 mg | 14.8 mg | 14.8 mg | 14.8 mg | 14.8 mg | 14.8 mg | 37 mg | 7.4 mg | 7.4 mg |
| Chlorobutanol | 0 mg | 0 mg | 0 mg | 0 mg | 0 mg | 0 mg | 0 mg | 0 mg | 0 mg | 0 mg |
| Glycerin | 14 g | 14 g | 1.4 g | 1.4 g | 1.4 g | 1.4 g | 1.4 g | 7 g | 1.4 g | 1.4 g |
| EDTA | 0 mg | 0 mg | 38 mg | 13 mg | 0 mg | 0 mg | 0 mg | 0 mg | 13 mg | 13 mg |
| Pectin, 55-65% Esterification, 6-12% Methoxylation | 0 mg | 0 mg | 0 mg | 0 mg | 50 mg | 0 mg | 0 mg | 0 mg | 0 mg | 0 mg |
| Pectin, 20-26% Esterification, 2-4% Methoxylation | 0 mg | 0 mg | 0 mg | 0 mg | 0 mg | 50 mg | 0 mg | 0 mg | 0 mg | 0 mg |
| Pectin, 55-65% Esterification, 6-12% Methoxylation, ≥74% Galacturonic Acid | 0 mg | 0 mg | 0 mg | 0 mg | 0 mg | 0 mg | 50 mg | 0 mg | 0 mg | 50 mg |
| NaOH/HCl | 4.1 | 4.1 | 4.1 | 4.1 | 4.1 | 4.1 | 4.1 | 4.1 | 4.1 | 4.1 |
| Purified Water | 1 L | 1 L | 100 mL | 100 mL | 100 mL | 100 mL | 100 mL | 500 mL | 100 mL | 100 mL |

FIG. 1

| Ingredient | Amount | | | | | | | | |
|---|---|---|---|---|---|---|---|---|---|
| **Naloxone HCl Dose (per 100 µL)** | 10 mg | 10 mg | 10 mg | 10 mg | 10 mg | 0 mg | 0 mg | 0 mg | 0 mg |
| **Naloxone HCl Dihydrate** | 109.9 g | 109.9 g | 109.9 g | 109.9 g | 109.9 g | 0g | 0 g | 0 g | 0 g |
| Citric Acid, Anhydrous | 85.7 mg | 85.7 mg | 85.7 mg | 85.7 mg | 85.7 mg | 85.7 mg | 85.7 mg | 0 mg | 171.4 mg |
| Trisodium Citrate Dihydrate | 148 mg | 148 mg | 148 mg | 148 mg | 148 mg | 148 mg | 148 mg | 0 mg | 296 mg |
| Chlorobutanol | 0 mg | 0 mg | 0 mg | 0 mg | 0 mg | 0 mg | 0 mg | 0 mg | 0 mg |
| Glycerin | 14 g | 14 g | 14 g | 14 g | 14 g | 14 g | 14 g | 0 g | 28 g |
| EDTA | 0 mg | 50 mg | 40 mg | 50 mg | 40 mg | 0 mg | 0 mg | 0 mg | 0 mg |
| Pectin, 55-65% Esterification, 6-12% Methoxylation | 0 mg | 0 mg | 0 mg | 100 mg | 100 mg | 100 mg | 0 mg | 0 mg | 0 mg |
| Pectin, 20-26% Esterification, 2-4% Methoxylation | 0 mg | 0 mg | 0 mg | 0 mg | 0 mg | 0 mg | 0 mg | 0 mg | 0 mg |
| Pectin, 55-65% Esterification, 6-12% Methoxylation, ≥74% Galacturonic Acid | 0 mg | 0 mg | 0 mg | 0 mg | 0 mg | 0 mg | 0 mg | 0 mg | 0 mg |
| NaOH/HCl | 4.1 | 4.1 | 4.1 | 4.1 | 4.1 | 4.1 | 4.1 | N/A | 4.1 |
| Purified Water | 1 L | 1 L | 1 L | 1 L | 1 L | 1 L | 1 L | 2 L | 2 L |
| Sodium Chloride | 0 g | 0 g | 0 g | 0 g | 0 g | 0 g | 0 g | 18 g | 0 g |

FIG. 2

| Ingredient | Amount | | | | | | | | |
|---|---|---|---|---|---|---|---|---|---|
| **Naloxone HCl Dose (per 100 µL)** | 10 mg | 10 mg | 10 mg | 10 mg | 8 mg | 8 mg | 9 mg | 10 mg | 9 mg |
| **Naloxone HCl Dihydrate** | 10.99 g | 10.99 g | 10.99 g | 10.99 g | 8.79 g | 8.79 g | 9.89 g | 10.99 g | 9.89 g |
| Citric Acid, Anhydrous | 32.7 mg | 56.5 mg | 50.9 mg | 49.7 mg | 53.7 mg | 50.9 mg | 50.3 mg | 49.7 mg | 0 mg |
| Trisodium Citrate Dihydrate | 38.2 mg | 60.6 mg | 69.2 mg | 71.0 mg | 64.9 mg | 69.2 mg | 70.1 mg | 71.0 mg | 440 mg |
| Glycerin | 1.4 g | 1.4 g | 1.4 g | 1.4 g | 1.4 g | 1.4 g | 1.4 g | 2.0 g | 2.3 g |
| NaOH/HCl | 4.2 | 4.2 | 4.2 | 4.2 | 4.2 | 4.2 | 4.2 | 4.2 | 4.1 |
| Purified Water | 100 mL | 100 mL | 100 mL | 100 mL | 100 mL | 100 mL | 100 mL | 100 mL | 100 mL |

FIG. 3

| Ingredient | Amount | | | | | | | | | |
|---|---|---|---|---|---|---|---|---|---|---|
| **Naloxone HCl Dose** | 12 mg | 12 mg | 12 mg | 12 mg | 12 mg | 12 mg | 12 mg | 12 mg | 12 mg | 12 mg |
| **Naloxone HCl Dihydrate** | 13.2 g | 13.2 g | 13.2 g | 13.2 g | 13.2 g | 13.2 g | 13.2 g | 13.2 g | 13.2 g | 13.2 g |
| Citric Acid, Anhydrous | 48.5 mg | 29.2 mg | 165.0 mg | 29.2 mg | 29.2 mg | 29.2 mg | 165.0 mg | 165.0 mg | 165.0 mg | 48.5 mg |
| Trisodium Citrate Dihydrate | 72.8 mg | 43.5 mg | 188.5 mg | 43.5 mg | 43.5 mg | 43.5 mg | 188.5 mg | 188.5 mg | 188.5 mg | 72.8 mg |
| Chlorobutanol | 100.0 mg | 0 mg | 200.0 mg | 200.0 mg | 0 mg | 200.0 mg | 0 mg | 200.0 mg | 0 mg | 0 mg |
| Glycerin | 1.4 g | 1.0 g | 2.3 g | 1.0 g | 2.3 g | 2.3 g | 1.0 g | 1.0 g | 2.3 g | 0 g |
| Propylene Glycol | 0 g | 0 g | 0 g | 0 g | 0 g | 0 g | 0 g | 0 g | 0 g | 2.0 g |
| Labrafil | 0 g | 0 g | 0 g | 0 g | 0 g | 0 g | 0 g | 0 g | 0 g | 0 g |
| Polyethylene Glycol 400 | 0 g | 0 g | 0 g | 0 g | 0 g | 0 g | 0 g | 0 g | 0 g | 0 g |
| NaOH/HCl | 4.2 | 4.2 | 4.2 | 4.2 | 4.2 | 4.2 | 4.2 | 4.2 | 4.2 | 4.2 |
| Purified Water | 100 mL | 100 mL | 100 mL | 100 mL | 100 mL | 100 mL | 100 mL | 100 mL | 100 mL | 100 mL |

FIG. 4

| Ingredient | Amount | | | | | | | | | |
|---|---|---|---|---|---|---|---|---|---|---|
| **Naloxone HCl Dose (per 100 µL)** | 12 mg | 12 mg | 12 mg | 12 mg | 10 mg | 10 mg | 10 mg | 10 mg | 10 mg | 10 mg |
| **Naloxone HCl Dihydrate** | 13.2 g | 13.2 g | 13.2 g | 13.2 g | 10.99 g | 10.99 g | 10.99 g | 10.99 g | 10.99 g | 10.99 g |
| Citric Acid, Anhydrous | 48.5 mg | 48.5 mg | 48.5 mg | 48.5 mg | 49.7 mg | 49.7 mg | 48.5 mg | 57.9 mg | 57.9 mg | 53.0 mg |
| Trisodium Citrate Dihydrate | 72.8 mg | 72.8 mg | 72.8 mg | 72.8 mg | 218.0 mg | 218.0 mg | 72.8 mg | 205.5 mg | 205.5 mg | 213.0 mg |
| Chlorobutanol | 0 mg | 0 mg | 0 mg | 0 mg | 0 mg | 0 mg | 200.0 mg | 200.0 mg | 200.0 mg | 0 mg |
| Glycerin | 0 g | 0 g | 0 g | 0 g | 1.4 g | 1.4 g | 1.4 g | 1.4 g | 1.4 g | 1.4 g |
| Propylene Glycol | 20.0 g | 0 g | 0 g | 0 g | 3.0 g | 0 g | 0 g | 0 g | 3.0 g | 0 g |
| Labrafil | 0 g | 1.0 g | 0 g | 0 g | 0 g | 0 g | 0 g | 0 g | 0 g | 0 g |
| Polyethylene Glycol 400 | 0 g | 0 g | 2.0 g | 20.0 g | 0 g | 10.0 g | 0 g | 3.0 g | 0 g | 3.0 g |
| NaOH/HCl | 4.2 | 4.2 | 4.2 | 4.2 | 4.2 | 4.2 | 4.2 | 4.2 | 4.2 | 4.2 |
| Purified Water | 100 mL | 100 mL | 100 mL | 100 mL | 100 mL | 100 mL | 100 mL | 100 mL | 100 mL | 100 |

FIG. 5

| **Ingredient** | **Amount** | | | | | | | | | |
|---|---|---|---|---|---|---|---|---|---|---|
| **Naloxone HCl Dose (per 100 µL)** | 12 mg | 12 mg | 10 mg | 10 mg | 0 mg | 10 mg | 10 mg | 10 mg | 11 mg | 11.3 mg |
| **Naloxone HCl Dihydrate** | 13.2 g | 13.2 g | 10.99 g | 109.9 g | 0 g | 109.9 g | 219.8 g | 10.99 g | 12.1 g | 12.4 g |
| Citric Acid, Anhydrous | 109.4 mg | 105 mg | 58 mg | 0 mg | 0 mg | 0 mg | 0 mg | 0 mg | 0 mg | 0 mg |
| Trisodium Citrate Dihydrate | 141 mg | 147 mg | 83 mg | 2951 mg | 2951 mg | 2955 mg | 5900 mg | 296 mg | 222 mg | 221 mg |
| Chlorobutanol | 0 mg | 0 mg | 0 mg | 0 mg | 0 mg | 0 mg | 0 mg | 0 mg | 0 mg | 0 mg |
| Glycerin | 1.4 g | 1.4 g | 1.4 g | 14 g | 14 g | 14 g | 28 g | 0 g | 1.4 g | 1.4 g |
| Propylene Glycol | 0 g | 3 g | 3 g | 30 g | 30 g | 30 g | 60 g | 0 g | 2 g | 1 g |
| Labrafil | 0 g | 0 g | 0 g | 0 g | 0 g | 0 g | 0 g | 0 g | 0 g | 0 g |
| Polyethylene Glycol 400 | 0 g | 0 g | 0 g | 0 g | 0 g | 0 g | 0 g | 0 g | 0 g | 0 g |
| NaOH/HCl | 4.2 | 4.2 | 4.2 | 4.2 | 4.2 | 4.2 | 4.2 | 4.2 | 4.2 | 4.2 |
| Purified Water | 100 mL | 100 mL | 100 mL | 1000 mL | 1000 mL | 1000 mL | 2000 mL | 100 mL | 100 mL | 100 mL |

FIG. 6

| Ingredient | Amount | | | | | | | | | |
|---|---|---|---|---|---|---|---|---|---|---|
| **Naloxone HCl Dose (per 100 µL)** | 11 mg | 10 mg | 10 Mg | 10 mg | 10 mg | 11 mg | 10 mg | 10 mg | 11 mg | 10 mg |
| **Naloxone HCl Dihydrate** | 12.1 g | 109.9 g | 11 g | 11 g | 11 g | 12 g | 11 g | 11 g | 12 g | 11 g |
| Citric Acid, Anhydrous | 0 mg | 0 mg | 0 mg | 0 mg | 0 mg | 0 mg | 0 mg | 0 mg | 0 mg | 0 mg |
| Trisodium Citrate Dihydrate | 223 mg | 2951 mg | 221 mg | 221 mg | 221 mg | 296 mg | 296 mg | 295 mg | 296 mg | 295 mg |
| Chlorobutanol | 0 mg | 0 mg | 0 mg | 0 mg | 0 mg | 0 mg | 0 mg | 0 mg | 0 mg | 0 mg |
| Glycerin | 1.4 g | 14 g | 1.4 g | 1.4 g | 1.4 g | 1.4 g | 1.4 g | 1.4 g | 1.4 g | 1.4 g |
| Propylene Glycol | 0 g | 0 g | 2 g | 1 g | 0 g | 0 g | 1 g | 2 g | 1.5 g | 1.5 g |
| Labrafil | 0 g | 0 g | 0 g | 0 g | 0 g | 0 g | 0 g | 0 g | 0 g | 0 g |
| Polyethylene Glycol 400 | 0 g | 0 g | 0 g | 0 g | 0 g | 0 g | 0 g | 0 g | 0 g | 0 g |
| NaOH/HCl | 4.2 | 4.2 | 4.2 | 4.2 | 4.2 | 4.2 | 4.2 | 4.2 | 4.2 | 4.2 |
| Purified Water | 100 mL | 1000 mL | 100 mL | 100 mL | 100 mL | 100 mL | 100 mL | 100 mL | 100 mL | 100 mL |

FIG. 7

| Ingredient | Amount | | | |
|---|---|---|---|---|
| **Naloxone HCl Dose (per 100 μL)** | 10 mg | 11 mg | 10 mg | 11 mg |
| **Naloxone HCl Dihydrate** | 11 g | 12 g | 11 g | 12 g |
| Citric Acid, Anhydrous | 0 mg | 0 mg | 0 mg | 0 mg |
| Trisodium Citrate Dihydrate | 296 mg | 296 mg | 296 mg | 296 mg |
| Chlorobutanol | 0 mg | 0 mg | 0 mg | 0 mg |
| Glycerin | 1.4 g | 1.4 g | 1.4 g | 1.4 g |
| Propylene Glycol | 2 g | 2 g | 2.5 g | 2.5 g |
| Labrafil | 0 g | 0 g | 0 g | 0 g |
| Polyethylene Glycol 400 | 0 g | 0 g | 0 g | 0 g |
| NaOH/HCl | 4.2 | 4.2 | 4.2 | 4.2 |
| Purified Water | 100 mL | 100 mL | 100 mL | 100 mL |

FIG. 8

| **Ingredient** | **Amount** | | | | | | | | | | | | |
|---|---|---|---|---|---|---|---|---|---|---|---|---|---|
| **Naloxone HCl Dose (per 110 µL)** | 10 mg | 10 mg | 10 mg | 10 mg | 10 mg | 10 mg | 10 mg | 0 mg | 0 mg | 4 mg | 12 mg | 12 mg | 12 mg |
| **Naloxone HCl Dihydrate** | 10.00 g | 50.00 g | 10.00 g | 49.96 g | 49.96 g | 49.96 g | 49.96 g | 0 g | 0 g | 21.98 g | 13.2 g | 13.2 g | 13.2 g |
| Trisodium Citrate Dihydrate | 221.2 mg | 1.475 g | 442.5 mg | 1.4705 g | 1.4705 g | 1.4705 g | 1.4705 g | 1.4705 g | 1.4705 g | 1.4705 g | 295 mg | 295 mg | 295 mg |
| Glycerin | 1.4 g | 7.0 g | 1.4 g | 7.0 g | 7.0 g | 7.0 g | 7.0 g | 7.0 g | 7.0 g | 7.0 g | 1.4 g | 1.4 g | 1.4 g |
| Propylene Glycol | 0 g | 0 g | 0 g | 0 g | 0 g | 0 g | 12.5 g | 0 g | 12.5 g | 0 g | 0 g | 0 g | 0 g |
| NaOH/HCl | 4.2 | 4.2 | 4.2 | 4.2 | 4.2 | 4.2 | 4.2 | 4.2 | 4.2 | 4.2 | 3.7 | 4.2 | 4.7 |
| Purified Water | 100 mL | 500 mL | 100 mL | 500 mL | 500 mL | 500 mL | 500 mL | 500 mL | 500 mL | 500 mL | 100 mL | 100 mL | 100 mL |

FIG. 9

DRUG PRODUCTS FOR INTRANASAL ADMINISTRATION AND USES THEREOF

CROSS-REFERENCE TO RELATED APPLICATIONS

This application is a continuation of U.S. application Ser. No. 17/882,014, filed Aug. 5, 2022, which is a continuation of International Application Number PCT/US2021/016873 filed Feb. 5, 2021, which claims priority to U.S. Provisional Application No. 62/970,629 filed Feb. 5, 2020, the contents of which are incorporated herein by reference.

BACKGROUND

Opioid receptors are G protein-coupled receptors (GPCRs) that are activated both by endogenous opioid peptides and by clinically important alkaloid analgesic drugs such as morphine. In the United States, mortality rates closely correlate with opioid sales. In 2008, approximately 36,450 people died from drug overdoses. At least 14,800 of these deaths involved prescription opioid analgesics. Moreover, according to the Substance Abuse and Mental Health Services Administration, the number/rate of Americans 12 years of age and older who currently abuse pain relievers has increased by 20 percent between 2002 and 2009.

Naloxone is an opioid receptor antagonist that is approved for use by injection for the reversal of opioid overdose and for adjunct use in the treatment of septic shock. It is currently being used mainly in emergency departments and in ambulances by trained medical professionals. There have been efforts to expand its use by providing the drug to some patients with take-home opioid prescriptions and those who inject illicit drugs, potentially facilitating earlier administration of the drug.

The Drug Overdose Prevention and Education (DOPE) Project was the first naloxone prescription program (NPP) established in partnership with a county health department (San Francisco Department of Public Health), and is one of the longest running NPPs in the USA. From September 2003 to December 2009, 1,942 individuals were trained and prescribed naloxone through the DOPE Project, of whom 24% returned to receive a naloxone refill, and 11% reported using naloxone during an overdose event. Of 399 overdose events where naloxone was used, participants reported that 89% were reversed. In addition, 83% of participants who reported overdose reversal attributed the reversal to their administration of naloxone, and fewer than 1% reported serious adverse effects.

Naloxone has a relatively short half-life compared to some longer-acting opioid formulations. After a typical therapeutic dose of naloxone is administered to an opioid overdose patient, there is often the need to re-administer naloxone, in some cases even several times, and it is important to seek immediate medical attention. Furthermore, it has been suggested that in view of the growing opioid overdose crisis in the US, naloxone should be made available over-the-counter (OTC). Thus, there remains a need for storage-stable formulations that can enable untrained individuals to quickly deliver a therapeutically effective dose of a rapid-acting opioid receptor antagonist to an opioid overdose patient. The formulations described herein meet this and other needs.

SUMMARY

Described herein, inter alia, are pharmaceutical compositions comprising an opioid receptor antagonist such as naloxone or a pharmaceutically acceptable salt thereof or a hydrate thereof, devices configured to administer said compositions, kits comprising said compositions and devices, and methods of using said compositions in the treatment of opioid overdoses and symptoms thereof.

In one embodiment, provided herein is a pharmaceutical composition comprising naloxone or a pharmaceutically acceptable salt thereof (e.g., naloxone hydrochloride) or a hydrate thereof (e.g., naloxone hydrochloride dihydrate) and a polyol (e.g., a polyol having a molecular weight less than 300 Da, e.g., propylene glycol or glycerin), wherein the composition is substantially free of a preservative. In another embodiment, provided herein are unit doses of the pharmaceutical compositions described herein.

In one embodiment, provided herein is a device configured for intranasal administration of a pharmaceutical composition described herein to a subject (e.g., a patient in need thereof), wherein the device is configured for delivery of one dose of the pharmaceutical composition to the subject.

In another embodiment, described herein is a device configured for intranasal administration of a pharmaceutical composition described herein to a subject (e.g., a patient in need thereof), wherein the device is configured for delivery of two doses of the pharmaceutical composition to the subject.

In another embodiment, provided herein is a device configured for intranasal administration of one occurrence of a unit dose described herein to a subject (e.g., a patient in need thereof), wherein the device is configured for a single delivery of the unit dose to the subject.

In another embodiment, provided herein is a device configured for intranasal administration of two independent occurrences of a unit dose described herein to a subject (e.g., a patient in need thereof), wherein the device is configured for a single delivery of each occurrence of the unit dose to the subject.

Additionally provided is a kit comprising the pharmaceutical composition described herein, unit dose described herein, or device described herein, and instructions for use in administering the composition to a patient suffering from an opioid overdose or symptom thereof.

Further provided, in another embodiment, is a method of treating an opioid overdose or symptom thereof in a patient in need thereof, comprising administering to the patient the pharmaceutical composition described herein or unit dose described herein. The pharmaceutical composition described herein or unit dose described herein may be administered from a device described herein.

Also provided herein, in one embodiment, is a process comprising the steps of: a. deoxygenating the pharmaceutical composition by sparging with nitrogen until the dissolved oxygen is NMT 1 ppm; b. filling a unit dose container with the pharmaceutical composition; c. removing oxygen from the head space gas of the unit dose container to provide a reduced oxygen head space unit dose container, then stoppering the unit dose container; and d. heating the deoxygenated unit dose container at a temperature of not more than 125° C.; thereby reducing bioburden of the pharmaceutical composition.

Also described herein, in another embodiment, is a process for sterilizing the pharmaceutical composition described herein or unit dose described herein, comprising the steps of: a. filling a unit dose container with the pharmaceutical composition; b. deoxygenating the unit dose container to provide a deoxygenated unit dose container; and c. heating the deoxygenated unit dose container at a temperature of not more than 125° C.; thereby sterilizing the pharmaceutical composition.

BRIEF DESCRIPTION OF THE DRAWINGS

FIG. 1 depicts exemplary formulations for evaluating different excipients and EDTA levels.

FIG. 2 depicts exemplary formulations for evaluating different excipients and EDTA levels.

FIG. 3 depicts exemplary formulations for evaluating different buffer strengths and 8-10 mg doses of 100 μL.

FIG. 4 depicts exemplary formulations for evaluating solubility with different buffer strengths, with and without a preservative.

FIG. 5 depicts exemplary formulations for evaluating solubility using various buffer strengths and excipients.

FIG. 6 depicts exemplary formulations for evaluating solubility with varying buffer strengths, with and without propylene glycol.

FIG. 7 depicts exemplary formulations comprising Naloxone HCl dihydrate and buffers with different strengths.

FIG. 8 depicts exemplary formulations comprising Naloxone HCl dihydrate and buffers with different strengths.

FIG. 9 depicts exemplary formulations with reduced concentration of Naloxone HCl dihydrate and increased delivery volume of the formulation, focused in on buffer strength.

DETAILED DESCRIPTION

Figure 10:
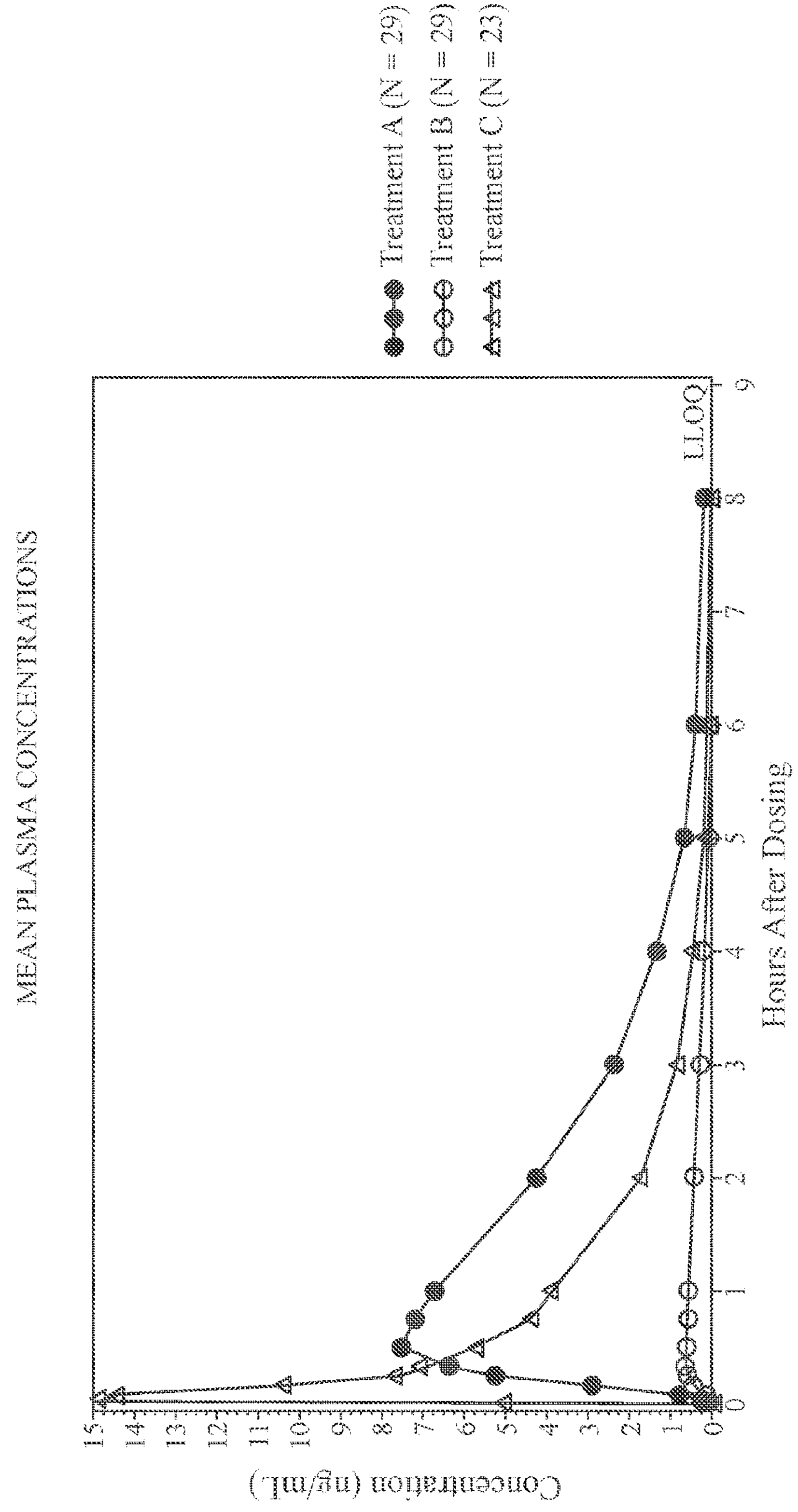
FIG. 10 depicts an overlay plot of mean plasma concentration of Naloxone over 0-8 hours measured for intranasal, intramuscular and intravenous administration of Naloxone HCl.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined herein, all technical and scientific terms used herein have the same meaning as commonly understood by one of ordinary skill in the art to which the subject matter pertains. All publications, patent applications, patents, and other references mentioned herein are incorporated by reference in their entirety.

Naloxone

Provided herein, in part, are drug products adapted for nasal delivery of naloxone or pharmaceutically acceptable salt thereof or hydrate there. Naloxone and its pharmaceutically acceptable salts thereof and hydrates thereof can act as opioid receptor antagonists.

Naloxone is commercially available as a hydrochloride salt. Naloxone hydrochloride (17-allyl-4,5a-epoxy-3,14-dihydroxymorphinan-6-one hydrochloride), a narcotic antagonist, is a synthetic congener of oxymorphone. In structure it differs from oxymorphone in that the methyl group on the nitrogen atom is replaced by an allyl group. Naloxone hydrochloride is an essentially pure narcotic antagonist, i.e., it does not possess the "agonistic" or morphine-like properties characteristic of other narcotic antagonists; naloxone does not produce respiratory depression, psychotomimetic effects or pupillary constriction. In the absence of narcotics or agonistic effects of other narcotic antagonists it exhibits essentially no pharmacologic activity. Naloxone has not been shown to produce tolerance or to cause physical or psychological dependence. In the presence of physical dependence on narcotics naloxone will produce withdrawal symptoms.

While the mechanism of action of naloxone is not fully understood, the preponderance of evidence suggests that naloxone antagonizes the opioid effects by competing for the same receptor sites. When naloxone hydrochloride is administered intravenously the onset of action is generally apparent within two minutes; the onset of action is only slightly less rapid when it is administered subcutaneously or intramuscularly. The duration of action is dependent upon the dose and route of administration of naloxone hydrochloride. Intramuscular administration produces a more prolonged effect than intravenous administration. The requirement for repeat doses of naloxone, however, will also be dependent upon the amount, type and route of administration of the narcotic being antagonized. Following parenteral administration naloxone hydrochloride is rapidly distributed in the body. It is metabolized in the liver, primarily by glucuronide conjugation, and excreted in urine. In one study, the serum half-life in adults ranged from 30 to 81 minutes (mean 64±12 minutes). In a neonatal study, the mean plasma half-life was observed to be 3.1±0.5 hours.

While many of the embodiments of the pharmaceutical compositions described herein will be described and exemplified with naloxone, other opioid receptor antagonists can be adapted for nasal delivery based on the teachings of the specification. In fact, one of ordinary skill in the art will appreciate from the teachings herein that the devices and pharmaceutical compositions described herein may be suitable for other opioid receptor antagonists. The opioid receptor antagonists described herein include μ-opioid receptor antagonists and δ-opioid receptor antagonists. Examples of useful opioid receptor antagonists include naloxone, naltrexone, methylnaltrexone, and nalmefene. Other useful opioid receptor antagonists are known (see, e.g., Kreek et al., U.S. Pat. No. 4,987,136).

Pharmaceutical Compositions

Provided herein, in part, are pharmaceutical compositions comprising an opioid receptor antagonist such as naloxone or a pharmaceutically acceptable salt thereof (e.g., naloxone hydrochloride) of hydrate thereof (e.g., naloxone hydrochloride dihydrate). In some embodiments, the opioid receptor antagonist is the only pharmaceutically active compound in said pharmaceutical composition. In some embodiments, said opioid receptor antagonist is naloxone hydrochloride. In some embodiments, said opioid receptor antagonist is naloxone hydrochloride dihydrate.

Some embodiments of the present invention include a method of producing a pharmaceutical composition comprising admixing naloxone or a pharmaceutically acceptable salt thereof of hydrate thereof and a pharmaceutically acceptable carrier. Pharmaceutical compositions described herein can be formulated for intranasal administration and, in one embodiment, are applied directly to the nasal cavity using the devices described herein. In the case of a spray, this may be achieved for example by means of a metering atomizing spray pump.

It has been found that the pharmaceutical compositions described herein can be subjected to a sterilization technique to produce drug products suitable for administration to a subject in need thereof. In a preferred embodiment, the sterilization technique is autoclave sterilization. In another preferred embodiment, the sterilization technique is terminal autoclaving (e.g. terminal autoclaving for bioburden reduction). The compositions subjected to such sterilization techniques can be substantially free of a preservative.

Liquid preparations such as the aqueous pharmaceutical compositions described herein can include solutions, suspensions and emulsions, for example, water, water-glycerin, or water-propylene glycol solutions. Additional ingredients in such liquid preparations may include: surfactants such as Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, and the like, and mixtures thereof; a tonicity agent such as: dextrose, lactose, sodium chloride, calcium chloride, magnesium chloride, sorbitol, sucrose, mannitol, trehalose, raffinose, polyethylene glycol, hydroxyethyl starch, glycine, and the like, and mixtures thereof; and a suspending agent such as microcrystalline cellulose, carboxymethylcellulose sodium NF, polyacrylic acid, magnesium aluminum silicate, xanthan gum, and the like, and mixtures thereof.

The opioid receptor antagonists described herein can be formulated into pharmaceutical compositions using techniques well known to those in the art. Suitable pharmaceutically acceptable excipients and carriers, outside those mentioned herein, are known in the art; for example, see Remington: The Science and Practice of Pharmacy, 21st ed., Lippincott Williams & Wilkins, Philadelphia, PA. (2005).

The opioid receptor antagonists, e.g., naloxone, described herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., Journal of Pharmaceutical Sciences, 66:1-19 (1977). Accordingly, a non-limiting example of a pharmaceutically acceptable salt described herein is naloxone hydrochloride. The acid addition salts may be obtained as the direct products of compound synthesis. In the alternative, the free base may be dissolved in a suitable solvent containing the appropriate acid and the salt isolated by evaporating the solvent or otherwise separating the salt and solvent. The opioid receptor antagonists described herein may form solvates with standard low molecular weight solvents using methods known to the skilled artisan.

Whenever a solution or mixture containing a pharmaceutically acceptable salt is mentioned, a pharmaceutically acceptable salt shall also encompass the dissolved form of the pharmaceutically acceptable salt (e.g., naloxone hydrochloride).

Whenever a solution or mixture containing a hydrate pharmaceutically acceptable salt is mentioned, a hydrate of a pharmaceutically acceptable salt shall also encompass the dissolved form of the hydrate of the pharmaceutically acceptable salt (e.g., naloxone hydrochloride dihydrate).

In an embodiment, a pharmaceutical composition described herein comprises naloxone or a pharmaceutically acceptable salt thereof or a hydrate thereof and a polyol, wherein the composition is substantially free of a preservative. The polyol can be, in one embodiment, a polyol having a molecular weight of less than 300 Da.

In some embodiments, the polyol is glycerin. In some embodiments, the composition comprises glycerin in an amount of about 1% to about 4% by weight based on the total weight of the composition. In some embodiments, the pharmaceutical composition comprises the glycerin in an amount of about 1% to about 2% by weight based on the total weight of the composition.

In the pharmaceutically acceptable compositions described herein, the pharmaceutically acceptable salt can be naloxone hydrochloride. In some embodiments, the composition comprises naloxone hydrochloride or hydrate thereof in an amount of about 4% to about 14% by weight based on the total weight of the composition. In some embodiments, the composition comprises naloxone hydrochloride or hydrate thereof in an amount of about 4% to about 12% by weight based on the total weight of the composition.

In some embodiments, the pharmaceutical composition described herein is an aqueous pharmaceutical composition. In some embodiments, said aqueous pharmaceutical composition is a solution. In some embodiments, such aqueous pharmaceutical compositions are free (e.g., substantially free) of particulate matter. In some embodiments, the pharmaceutical composition comprises water in an amount from about 85% to about 90% by weight based on the total weight of the composition.

The described pharmaceutical compositions can be substantially free of a preservative, wherein the preservative is present in an amount of no more than 2% by weight, no more than 1.5% by weight, no more than 1% by weight, no more than 0.5% by weight, no more than 0.1% by weight, no more than 0.01% by weight, no more than 0.001% by weight, or no more than 0.0001% by weight based on the total weight of the composition. Examples of such preservatives include, but are not limited to, chlorobutanol, benzalkonium chloride, methylparaben, sodium benzoate, benzoic acid, benzyl alcohol, phenyl ethyl alcohol, and combinations thereof.

The pharmaceutical compositions of the present disclosure may further comprise an additional polyol having a molecular weight of less than 300 Da. In some embodiments, the composition comprises the additional polyol in an amount of about 2% to about 4% by weight based on the total weight of the composition. In some embodiments, the additional polyol is propylene glycol. The described pharmaceutical compositions of the present disclosure may further comprise a buffer, a non-limiting example of which can be a citrate buffer. In some embodiments, the composition comprises the buffer in an amount from about 0.01% to about 0.4% by weight based on the total weight of the composition. The pharmaceutical compositions described herein may further comprise a stabilizing agent. The stabilizing agent, in some embodiments, can be selected from the group consisting of EDTA and disodium ETDA. The pharmaceutical composition can yet further comprise other excipients such as lipid-based excipients and polysaccharide-based excipients. A non-limiting example of a lipid-based excipient includes LABRAFIL®, whereas a non-limiting example of a polysaccharide-based excipient is pectin.

The present disclosure also provides aqueous pharmaceutical compositions comprising naloxone hydrochloride and glycerin, wherein the aqueous pharmaceutical composition is substantially free of a preservative. In one embodiment, described herein is an aqueous pharmaceutical composition comprising naloxone hydrochloride in an amount of about 4% to about 6% by weight based on the total weight of the aqueous pharmaceutical composition and glycerin in an amount of about 1% to about 2% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 4% to about 5% by weight based on the total weight of the aqueous pharmaceutical composition and glycerin in an amount of about 1% to about 2% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 4% by weight based on the total weight of the aqueous pharmaceutical composition and glycerin in an amount of about 1.5% to about 1.4% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 4% by weight based on the total weight of the aqueous pharmaceutical composition and glycerin in an amount of about 1.4% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 8% to about 11% by weight based on the total weight of the aqueous pharmaceutical composition, glycerin in an amount of about 1% to about 1.5% by weight based on the total weight of the aqueous pharmaceutical composition and propylene glycol in an amount of about 2% to about 3% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 11% by weight based on the total weight of the aqueous pharmaceutical composition, glycerin in an amount of about 1.2% to about 1.3% by weight based on the total weight of the aqueous pharmaceutical composition, and propylene glycol in an amount of about 2.9% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 11% by weight based on the total weight of the aqueous pharmaceutical composition, glycerin in an amount of about 1.3% by weight based on the total weight of the aqueous pharmaceutical composition, and propylene glycol in an amount of about 2.9% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 8% to about 11% by weight based on the total weight of the aqueous pharmaceutical composition and glycerin in an amount of about 1% to about 2% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 8% to about 11% by weight based on the total weight of the aqueous pharmaceutical composition and glycerin in an amount of about 1.3% to about 1.4% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 10% by weight based on the total weight of the aqueous pharmaceutical composition and glycerin in an amount of about 1.4% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 8% to about 11% by weight based on the total weight of the aqueous pharmaceutical composition and glycerin in an amount of about 1% to about 2% by weight based on the total weight of the aqueous pharmaceutical composition, wherein the aqueous pharmaceutical composition is substantially free of a preservative.

In one embodiment, described herein is an aqueous pharmaceutical composition comprising naloxone hydrochloride in an amount of about 10% by weight based on the total weight of the aqueous pharmaceutical composition and glycerin in an amount of about 1.4% by weight based on the total weight of the aqueous pharmaceutical composition, wherein the aqueous pharmaceutical composition is substantially free of a preservative.

Further provided herein are aqueous pharmaceutical compositions comprising naloxone hydrochloride, glycerin, and a citrate buffer. In one embodiment, described herein is an aqueous pharmaceutical composition comprising naloxone hydrochloride in an amount of about 4% to about 6% by weight based on the total weight of the aqueous pharmaceutical composition, glycerin in an amount of about 1% to about 2% by weight based on the total weight of the aqueous pharmaceutical composition, and a citrate buffer in an amount of about 0.2% to about 0.4% by weight based on the total weight of the aqueous pharmaceutical composition.

In one embodiment, described herein is an aqueous pharmaceutical composition comprising naloxone hydrochloride in an amount of about 4% to about 5% by weight based on the total weight of the aqueous pharmaceutical composition, glycerin in an amount of about 1% to about 2% by weight based on the total weight of the aqueous pharmaceutical composition, and a citrate buffer in an amount of about 0.2% to about 0.4% by weight based on the total weight of the aqueous pharmaceutical composition.

In one embodiment, described herein is an aqueous pharmaceutical composition comprising naloxone hydrochloride in an amount of about 4% by weight based on the total weight of the aqueous pharmaceutical composition, glycerin in an amount of about 1.5% to about 1.4% by weight based on the total weight of the aqueous pharmaceutical composition, and a citrate buffer in an amount of about 0.2% to about 0.3% by weight based on the total weight of the aqueous pharmaceutical composition.

In one embodiment, described herein is an aqueous pharmaceutical composition comprising naloxone hydrochloride in an amount of about 4% by weight based on the total weight of the aqueous pharmaceutical composition, glycerin in an amount of about 1.4% by weight based on the total weight of the aqueous pharmaceutical composition, and a citrate buffer in an amount of about 0.2% to about 0.3% by weight based on the total weight of the aqueous pharmaceutical composition.

In one embodiment, described herein is an aqueous pharmaceutical composition comprising naloxone hydrochloride in an amount of about 8% to about 11% by weight based on the total weight of the aqueous pharmaceutical composition, glycerin in an amount of about 1% to about 1.5% by weight based on the total weight of the aqueous pharmaceutical composition, propylene glycol in an amount of about 2% to about 3% by weight based on the total weight of the aqueous pharmaceutical composition, and a citrate buffer in an amount of about 0.2% to about 0.4% by weight based on the total weight of the aqueous pharmaceutical composition.

In one embodiment, described herein is an aqueous pharmaceutical composition comprising naloxone hydrochloride in an amount of about 11% by weight based on the total weight of the aqueous pharmaceutical composition, glycerin in an amount of about 1.2% to about 1.3% by weight based on the total weight of the aqueous pharmaceutical composition, propylene glycol in an amount of about 2.9% by weight based on the total weight of the aqueous pharmaceutical composition, and a citrate buffer in an amount of about 0.2% to about 0.3% by weight based on the total weight of the aqueous pharmaceutical composition.

In one embodiment, described herein is an aqueous pharmaceutical composition comprising naloxone hydrochloride in an amount of about 11% by weight based on the total weight of the aqueous pharmaceutical composition, glycerin in an amount of about 1.3% by weight based on the total weight of the aqueous pharmaceutical composition, propylene glycol in an amount of about 2.9% by weight based on the total weight of the aqueous pharmaceutical composition, and a citrate buffer in an amount of about 0.2% to about 0.3% by weight based on the total weight of the aqueous pharmaceutical composition.

In one embodiment, described herein is an aqueous pharmaceutical composition comprising naloxone hydrochloride in an amount of about 8% to about 11% by weight based on the total weight of the aqueous pharmaceutical composition, glycerin in an amount of about 1% to about 2% by weight based on the total weight of the aqueous pharmaceutical composition, and a citrate buffer in an amount of about 0.2% to about 0.4% by weight based on the total weight of the aqueous pharmaceutical composition.

In one embodiment, described herein is an aqueous pharmaceutical composition comprising naloxone hydrochloride in an amount of about 8% to about 11% by weight based on the total weight of the aqueous pharmaceutical composition, glycerin in an amount of about 1.3% to about 1.4% by weight based on the total weight of the aqueous pharmaceutical composition, and a citrate buffer in an amount of about 0.2% to about 0.4% by weight based on the total weight of the aqueous pharmaceutical composition.

In one embodiment, described herein is an aqueous pharmaceutical composition comprising naloxone hydrochloride in an amount of about 10% by weight based on the total weight of the aqueous pharmaceutical composition, glycerin in an amount of about 1.4% by weight based on the total weight of the aqueous pharmaceutical composition, and a citrate buffer in an amount of about 0.2% to about 0.3% based on the total weight of the aqueous pharmaceutical composition.

In one embodiment, described herein is an aqueous pharmaceutical composition comprising naloxone hydrochloride in an amount of about 8% to about 11% by weight based on the total weight of the aqueous pharmaceutical composition, glycerin in an amount of about 1% to about 2% by weight based on the total weight of the aqueous pharmaceutical composition, a citrate buffer in an amount of about 0.01% to about 0.03% by weight based on the total weight of the aqueous pharmaceutical composition.

In one embodiment, described herein is an aqueous pharmaceutical composition comprising naloxone hydrochloride in an amount of about 10% by weight based on the total weight of the aqueous pharmaceutical composition, glycerin in an amount of about 1.4% by weight based on the total weight of the aqueous pharmaceutical composition, and a citrate buffer in an amount of about 0.01% to about 0.03% by weight based on the total weight of the aqueous pharmaceutical composition.

In one embodiment, an aqueous pharmaceutical composition described herein is a solution. In an embodiment, the solution is substantially free of particulate matter. Furthermore, in another embodiment, an aqueous pharmaceutical composition described herein comprises water in an amount from about 85% to about 90% by weight based on the total weight of the aqueous pharmaceutical composition.

In an embodiment, the aqueous pharmaceutical compositions described herein are substantially free of a preservative. The preservatives in the aqueous pharmaceutical compositions described herein can be present, in one embodiment, in an amount of no more than 2% by weight, no more than 1.5% by weight, no more than 1% by weight, no more than 0.5% by weight, no more than 0.1% by weight, no more than 0.01% by weight, no more than 0.001% by weight, or no more than 0.0001% by weight based on the total weight of the composition. Examples of such preservatives include, but are not limited to, chlorobutanol, benzalkonium chloride, methylparaben, sodium benzoate, benzoic acid, benzyl alcohol, phenyl ethyl alcohol, or combinations thereof.

In one embodiment, a pharmaceutical composition described herein, such as an aqueous pharmaceutical composition described herein, including but not limited to where the aqueous pharmaceutical composition is a solution, is a sterilized pharmaceutical composition. In some embodiments, the pharmaceutical composition is sterilized using autoclave sterilization. In some embodiments, the pharmaceutical composition is sterilized using terminal autoclaving. In some embodiments, the pharmaceutical composition is terminally autoclaved for bioburden reduction.

The pharmaceutical compositions described herein can also be provided in various volumes. In some embodiments, a pharmaceutical composition described herein has a total volume of about 50 μL to about 250 μL. In some embodiments, a pharmaceutical composition described herein has a total volume of about 50 μL to about 200 μL. In some embodiments, a pharmaceutical composition described herein has a total volume of about 80 μL to about 120 μL. In some embodiments, a pharmaceutical composition described herein has a total volume of about 100 μL. In some embodiments, a pharmaceutical composition described herein has a total volume of about 110 μL.

The aqueous pharmaceutical compositions described herein can have a pH below 7. In some embodiments, the pH of the aqueous pharmaceutical composition is from about 3.5 to about 4.7. In some embodiments, the pH of the aqueous pharmaceutical composition is from about 4 to about 4.7. In some embodiments, the pH of the aqueous pharmaceutical composition is from about 4 to about 4.5. In some embodiments, the pH of the aqueous pharmaceutical composition is from about 4.2 to about 4.4. In some embodiments, the pH of the aqueous pharmaceutical composition is about 4.3.

Alternatively, the aqueous pharmaceutical compositions described herein can have a pH above 7. In some embodiments, the pH of the aqueous pharmaceutical composition is up to about 8. In some embodiments, the pH of the aqueous pharmaceutical composition is from about 7.5 to about 8.

In some embodiments, the osmolality of an aqueous pharmaceutical composition described herein is about 500 mOsm/kg to about 600 mOsm/kg. In some embodiments, the osmolality of an aqueous pharmaceutical composition described herein is about 500 mOsm/kg to about 560 mOsm/kg. In some embodiments, the osmolality of an aqueous pharmaceutical composition described herein is about 550 mOsm/kg to about 560 mOsm/kg. In some embodiments, the osmolality of an aqueous pharmaceutical composition described herein is about 555 mOsm/kg to about 565 mOsm/kg.

The pharmaceutical compositions described herein can comprise a stabilizing agent such as EDTA or a pharmaceutically acceptable salt thereof (e.g., sodium EDTA, which includes disodium, trisodium, or tetrasodium EDTA). Exemplary weight percentages based on the total weight of the pharmaceutical composition include, but are not limited to, about 0.01% to about 0.1%, about 0.01% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2%, about 2% to about 3%, about 3% to about 4%, about 4% to about 5%, about 5% to about 6%, about 6% to about 7%, about 7% to about 8%, about 8% to about 9%, and about 9% to about 10%.

The pharmaceutical compositions described herein can comprise a polysaccharide-based excipient such as pectin. Exemplary weight percentages based on the total weight of the pharmaceutical composition include, but are not limited to, about 0.01% to about 0.1%, about 0.01% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2%, about 2% to about 3%, about 3% to about 4%, about 4% to about 5%, about 5% to about 6%, about 6% to about 7%, about 7% to about 8%, about 8% to about 9%, and about 9% to about 10%.

The pharmaceutical compositions described herein can comprise a lipid-based excipient such as oleoyl polyoxyl-6 glycerides (e.g., LABRAFIL®). Exemplary weight percentages based on the total weight of the pharmaceutical composition include, but are not limited to, about 0.01% to about 0.1%, about 0.01% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2%, about 2% to about 3%, about 3% to about 4%, about 4% to about 5%, about 5% to about 6%, about 6% to about 7%, about 7% to about 8%, about 8% to about 9%, and about 9% to about 10%.

In some embodiments, the pharmaceutical composition maintains at least 99 wt % of the Naloxone HCl upon storage under the conditions of 25° C. for at least 1 month. In some embodiments, the pharmaceutical composition maintains at least 99 wt % of the Naloxone HCl upon storage under the conditions of 25° C. for at least 3 months. In some embodiments, the pharmaceutical composition maintains at least 99 wt % of the Naloxone HCl upon storage under the conditions of 25° C. for at least 6 months. In some embodiments, the pharmaceutical composition maintains at least 99 wt % of the Naloxone HCl upon storage under the conditions of 25° C. for at least 9 months. In some embodiments, the pharmaceutical composition maintains at least 98 wt % of the Naloxone HCl upon storage under the conditions of 40° C. for at least 1 month. In some embodiments, the pharmaceutical composition maintains at least 98 wt % of the Naloxone HCl upon storage under the conditions of 40° C. for at least 3 months. In some embodiments, the pharmaceutical composition maintains at least 98 wt % of the Naloxone HCl upon storage under the conditions of 40° C. for at least 6 months. In some embodiments, the pharmaceutical composition maintains at least 98 wt % of the Naloxone HCl upon storage under the conditions of 40° C. for at least 9 months. In some embodiments, the pharmaceutical composition is stable at 25° C. In some embodiments, the pharmaceutical composition is stable at 40° C.

Polyols

The pharmaceutical compositions of the present disclosure can generally comprise one or more polyols (e.g., polyols having a molecular weight of less than 300 Da), which include and are not limited to short-chain alkylene glycols (e.g., propylene glycol), glycerin, and polyethylene glycols.

The pharmaceutical compositions described herein can comprise glycerin. In one embodiment, glycerin is added to the pharmaceutical compositions to limit the formation of small droplets (e.g., droplets with a diameter less than 10 microns) of the composition upon administration to a patient in need thereof, increase the droplet residence time in the nasal mucosa or to prevent nasal dryness that could result from intranasal administration of the formulation. Glycerin can also be added to the pharmaceutical compositions to increase the solubility of the naloxone hydrochloride or hydrate thereof in the formulations described herein.

The pharmaceutical compositions described herein (e.g., aqueous pharmaceutical compositions described herein) can also comprise other water-soluble polyols. Other water soluble polyols include those having molecular weights of from about 40 to about 2000, such as from about 50 to about 500 or from about 58 to about 200 and can comprise multiple hydroxyl groups (i.e., from about 2 to about 6 hydroxyl groups). Water-soluble polyols suitable for inclusion herein as solubilizing agents are selected from glycerin, propylene glycol, hexylene glycol, mannitol, polyethylene glycol (e.g., polyethylene glycol 300, polyethylene glycol 350, and polyethylene glycol 400), sorbitol, polyethylene glycol and propylene glycol ethers of methyl glucose (e.g. ethyl glucam E-20 and propylglucam P-10), polyethylene glycol and propylene glycol ethers of lanolin alcohol (e.g. Solulan-75), and mixtures thereof.

Further, the pharmaceutical compositions described herein can comprise ethers of the polyols described herein, such as diethylene glycol monomethyl ether.

The polyols or ethers thereof described herein can exist in various weight percentages in the pharmaceutical compositions described herein. Exemplary weight percentages based on the total weight of the pharmaceutical composition include, but are not limited to, about 0.01% to about 0.1%, about 0.01% to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2%, about 2% to about 3%, about 3% to about 4%, about 4% to about 5%, about 5% to about 6%, about 6% to about 7%, about 7% to about 8%, about 8% to about 9%, about 9% to about 10%, about 10% to about 20%, about 20% to about 30%, about 30% to about 40%, and about 40% to about 50%.

Unit Doses

Also provided herein are unit doses of the pharmaceutical compositions described herein. In some embodiments, the unit dose is that of an aqueous pharmaceutical composition described herein. The unit doses described herein can be provided in different volumes to provide certain doses of an opioid receptor antagonist such as naloxone hydrochloride. In an embodiment, a unit dose can have a volume of about 50 μL to about 250 μL. In some embodiments, the unit dose can have a volume of about 50 μL to about 200 μL. In some embodiments, the unit dose can have a volume of about 80 μL to about 120 μL. In some embodiments, the unit dose can have a volume of about 100 μL. In some embodiments, the unit dose can have a volume of about 110 μL.

In some embodiments, the unit dose maintains at least 99 wt % of the Naloxone HCl upon storage under the conditions of 25° C. for at least 1 month. In some embodiments, the unit dose maintains at least 99 wt % of the Naloxone HCl upon storage under the conditions of 25° C. for at least 3 months. In some embodiments, the unit dose maintains at least 99 wt % of the Naloxone HCl upon storage under the conditions of 25° C. for at least 6 months. In some embodiments, the unit dose maintains at least 99 wt % of the Naloxone HCl upon storage under the conditions of 25° C. for at least 9 months. In some embodiments, the unit dose maintains at least 98 wt % of the Naloxone HCl upon storage under the conditions of 40° C. for at least 1 month. In some embodiments, the unit dose maintains at least 98 wt % of the Naloxone HCl upon storage under the conditions of 40° C. for at least 3 months. In some embodiments, the unit dose maintains at least 98 wt % of the Naloxone HCl upon storage under the conditions of 40° C. for at least 6 months. In some embodiments, the unit dose maintains at least 98 wt % of the Naloxone HCl upon storage under the conditions of 40° C. for at least 9 months. In some embodiments, the unit dose is stable at 25° C. In some embodiments, the unit dose is stable at 40° C.

Nasal Drug Delivery Devices and Kits

Also provided are nasal drug delivery devices comprising a pharmaceutical composition described herein or unit dose described herein. Nasal delivery is considered an attractive route for needle-free, systemic drug delivery, especially when rapid absorption and effect are desired. In addition, nasal delivery may help address issues related to poor bioavailability, slow absorption, drug degradation, and adverse events (AEs) in the gastrointestinal tract and avoids the first-pass metabolism in the liver.

Some EMS programs have developed a system using existing technologies of an approved drug and an existing medical device to administer naloxone intranasally, albeit in a non-FDA approved manner This has been accomplished by using the injectable formulation (1 mg/mL) and administering 1 mL per nostril via a marketed nasal atomizer/nebulizer device. The system combines an FDA-approved naloxone injection product (with a Luer fitted tip, no needles) with a marketed, medical device called the Mucosal Atomization Device (MAD™ Nasal, Wolfe Tory Medical, Inc.). This initiative is consistent with the U.S. Needlestick Safety and Prevention Act (Public Law 106-430). The EMS programs recognize limitations of this system, one limitation being that it is not assembled and ready-to-use. Although this administration mode appears to be effective in reversing narcosis, the formulation is not concentrated for retention in the nasal cavity. The 1 mL delivery volume per nostril is larger than that generally utilized for intranasal drug administration. Therefore, there is loss of drug from the nasal cavity, due either to drainage into the nasopharynx or externally from the nasal cavity. The devices described herein are improved products formulated for nasal delivery.

The devices described herein can be configured for intranasal administration to a patient (e.g., a patient suffering from an opioid overdose or symptom thereof). Liquid intranasal formulations are mainly aqueous solutions, but suspensions and emulsions can also be delivered. For example, in traditional spray pump systems, antimicrobial preservatives are typically required to maintain microbiological stability in liquid formulations. However, the drug delivery devices described herein do not require that the pharmaceutical compositions comprise a preservative. For example, the compositions can be substantially free of a preservative.

The devices configured for intranasal administration described herein can be configured for delivery of doses of a pharmaceutical composition described herein or unit dose described herein to a patient (e.g., a patient suffering from an opioid overdose or symptom thereof described herein).

In one embodiment, provided herein is a device configured for intranasal administration of a pharmaceutical composition described herein to a subject (e.g., a patient in need thereof), wherein the device is configured for delivery of one dose of the pharmaceutical composition to the subject.

In another embodiment, described herein is a device configured for intranasal administration of a pharmaceutical composition described herein to a subject (e.g., a patient in need thereof), wherein the device is configured for delivery of two doses of the pharmaceutical composition to the subject. In another embodiment, provided herein is a device configured for intranasal administration of one occurrence of a unit dose described herein to a subject (e.g., a patient in need thereof), wherein the device is configured for a single delivery of the unit dose to the subject. In another embodiment, provided herein is a device configured for intranasal administration of two independent occurrences of a unit dose described herein to a subject (e.g., a patient in need thereof), wherein the device is configured for a single delivery of each occurrence of the unit dose to the subject.

In some embodiments, the pharmaceutical composition or unit dose in the devices described herein is formulated for intranasal administration. In some embodiments, the dose (e.g., a unit dose) is contained in a single reservoir. In some embodiments, a device described herein is adapted for single use. In some embodiments, a device described herein is configured for delivery of the dose to a patient (e.g., a patient suffering from an opioid overdose or symptom thereof described herein) by a single actuation. In some embodiments, a device described herein is configured for delivery of the dose to a patient (e.g., a patient suffering from an opioid overdose or symptom thereof described herein) by more than one actuation. In some embodiments, a device described herein is not primed prior to administering the pharmaceutical composition or unit dose to the patient. In some embodiments, the pharmaceutical composition in a device described herein is sterilized (e.g., by autoclave sterilization, or by terminal autoclaving for bioburden reduction). In some embodiments, the unit dose in a device described herein is sterilized (e.g., by autoclave sterilization, or by terminal autoclaving for bioburden reduction). In some embodiments, a device described herein is filled with the pharmaceutical composition using aseptic filling. In some embodiments, a device described herein is filled with one or more unit doses using aseptic filling.

In some embodiments, the subject is a non-mammal In some embodiments, the subject is a mammal. In some embodiments, the subject is a human. In some embodiments, the subject is a patient in need thereof (e.g., a human patient in need thereof). In some embodiments, the patient in need thereof is suffering from an opioid overdose or symptom thereof (e.g., a human patient suffering from an opioid overdose or symptom thereof).

The devices described herein may also be filled with various volumes of a pharmaceutical composition described herein or unit dose described herein. In some embodiments, the pharmaceutical composition has a total volume of about 50 μL to about 250 μL. In some embodiments, the pharmaceutical composition has a total volume of about 50 μL to about 200 μL. In some embodiments, the pharmaceutical composition has a total volume of about 80 μL to about 120 μL. In some embodiments, the pharmaceutical composition has a total volume of about 100 μL. In some embodiments, the pharmaceutical composition has a total volume of about 110 μL.

In some embodiments, each unit dose has a total volume of about 50 μL to about 250 μL. In some embodiments, each unit dose has a total volume of about 50 μL to about 200 μL. In some embodiments, each unit dose has a total volume of about 80 μL to about 120 μL. In some embodiments, each unit dose has a total volume of about 100 μL. In some embodiments, each unit dose has a total volume of about 110 μL.

Alternatively, the devices configured for intranasal administration can be configured for delivery of two doses of a pharmaceutical composition described herein or unit dose described herein to a patient (e.g., a patient suffering from an opioid overdose or symptom thereof described herein). In some embodiments, the device is not primed prior to administering the dose to the patient.

In some embodiments, the device is actuatable with one hand. In some embodiments, the device is configured such that the 90% confidence interval for dose (e.g., a unit dose) delivered per actuation is ±about 2%. In some embodiments, the device is configured such that the 95% confidence interval for dose (e.g., a unit dose) delivered per actuation is ±about 2.5%. In some embodiments, the device is configured such that the delivery time is less than about 25 seconds. In some embodiments, the device is configured such that the delivery time is less than about 20 seconds.

In some embodiments, said single actuation yields a plasma concentration of ≥0.2 ng/mL within 2.5 minutes in said patient. In some embodiments, said single actuation yields a plasma concentration of ≥1 ng/mL within 5 minutes in said patient. In some embodiments, said single actuation yields a plasma concentration of ≥3 ng/mL within 10 minutes in said patient. In some embodiments, said single actuation yields a plasma concentration of ≥0.2 ng/mL within 2.5 minutes in said patient. In some embodiments, said single actuation yields a plasma concentration of ≥1 ng/mL within 5 minutes in said patient. In some embodiments, the patient is a mammal. In some embodiments, the patient is a human. In some embodiments, said patient is an opioid overdose patient or a suspected opioid overdose patient.

In one embodiment, a device described herein can be a metered-dose spray pump. Metered-dose spray pumps may require priming and some degree of overfill to maintain dose conformity for the labeled number of doses. They are well suited for drugs to be administered daily over a prolonged duration, but due to the priming procedure and limited control of dosing, they are less suited for drugs with a narrow therapeutic window. For expensive drugs and vaccines intended for single administration or sporadic use and where tight control of the dose and formulation is of particular importance, single-dose or bi-dose spray devices are preferred. A simple variant of a single-dose spray device (MAD™) is offered by LMA. A nosepiece with a spray tip is fitted to a standard syringe. The liquid drug to be delivered is first drawn into the syringe and then the spray tip is fitted onto the syringe. This device has been used in academic studies to deliver, for example, a topical steroid in patients with chronic rhinosinusitis and in a vaccine study. A pre-filled device based on the same principle for one or two doses (ACCUSPRAY™) is used to deliver the influenza vaccine FluMist, approved for both adults and children in the US market. A similar device for two doses was marketed by a Swiss company for delivery of another influenza vaccine a decade ago. The single- and bi-dose devices mentioned above consist of a reservoir, a piston, and a swirl chamber (see, e.g., the UDS UnitDose and BDS BiDose devices from Aptar, formerly Pfeiffer). The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like Imitrex and Zomig and the marketed influenza vaccine Flu-Mist (Becton Dickinson single-dose spray device) are delivered with this type of device.

The devices described herein can also be filled with a pharmaceutical composition via aseptic filling. With aseptic filling, the use of preservatives is not required, but overfill can be required resulting in a waste fraction similar to the metered-dose, multi-dose sprays. To emit 100 μL, a volume of 125 μL is filled in the device (Pfeiffer/Aptar single-dose device) used for the intranasal migraine medications Imitrex (sumatriptan) and Zomig (zolmitriptan) and about half of that for a bi-dose design. Sterile drug products may be produced using aseptic processing or terminal sterilization. Terminal sterilization usually involves filling and sealing product containers under high-quality environmental conditions. Products are filled and sealed in this type of environment to minimize the microbial and particulate content of the in-process product and to help ensure that the subsequent sterilization process is successful. In most cases, the product, container, and closure have low bioburden, but they are not sterile. The product in its final container is then subjected to a sterilization process such as heat or irradiation. In an aseptic process, the drug product, container, and closure are first subjected to sterilization methods separately, as appropriate, and then brought together. Because there is no process to sterilize the product in its final container, it is critical that containers be filled and sealed in an extremely high-quality environment. Aseptic processing involves more variables than terminal sterilization. Before aseptic assembly into a final product, the individual parts of the final product are generally subjected to various sterilization processes. For example, glass containers are subjected to dry heat; rubber closures are subjected to moist heat; and liquid dosage forms are subjected to filtration. Each of these manufacturing processes requires validation and control.

Devices described herein can be used after a patient receives tamper-proof and tamper-resistant compositions comprising an opioid agonist. Tamper-proof and tamper-resistant formulating technologies have been developed for safer delivery of opioid agonists, but such formulations are still abused resulting in opioid overdose. One such technology (Abuse Deterrent Prolonged Release Erosion Matrix (ADPREM); Egalet) utilizes a water-degradable polymer matrix technology that erodes from the surface at a constant rate. The matrix consists of one or more plasticizing polymers that cannot be crushed or melted. Another such technology (Abuse Resistant Technology (ART); Elite Laboratories) utilizes a proprietary coating technology consisting of various polymers that can sequester an opioid receptor antagonist (naltrexone) in fragile micropellets that are indistinguishable from the pellets containing the opioid. The formulation is designed to release sequestered antagonist only if the dosage is crushed or otherwise damaged for extraction. Oral dosage forms are prepared by coating powders, crystals, granules, or pellets with various polymers to impart different characteristics. The formulations can release the active drug in both immediate and sustained release form. Chronodelivery formulations using this technology can effectively delay drug absorption for up to five hours. Aversion (Acura Pharmaceuticals) utilizes certain proprietary combinations of functional excipients (e.g., gelling agents) and active ingredients intended to discourage the most common methods of prescription drug misuse and abuse. Ingredients may include nasal irritants (e.g., capsaicin) and aversive agents (e.g., niacin). In some embodiments, the opioid receptor agonist is provided in a tamper-proof formulation. In some embodiments, the opioid receptor agonist is in a tamper-resistant formulation. In some embodiments, the opioid receptor agonist is provided in a product selected from ACUROX® Oxycodone DETERx®, Egalet hydrocodone, Egalet morphine, Egalet oxycodone, EXALGO®, OPANA®, and REMOXY®.

In some embodiments, a person other than the patient suffering from an opioid overdose or symptom thereof administers the dose (e.g., a unit dose) to the patient. In some embodiments, the patient suffering from an opioid overdose or symptom thereof self-administers the dose (e.g., a unit dose).

In some embodiments, the pharmaceutical composition or unit dose is sterilized using terminal autoclaving. In some embodiments, the pharmaceutical composition or unit dose is terminally autoclaved for bioburden reduction.

Also provided are devices for "combination-therapy" comprising pharmaceutical compositions comprising at least one opioid receptor antagonist described herein, together with at least one known pharmaceutical agent and a pharmaceutically acceptable carrier.

Spray Characterization

The droplet size distribution of a nasal spray is a critical parameter, since it significantly influences the in vivo deposition of the drug in the nasal cavity. The droplet size is influenced by the actuation parameters of the device and the formulation. The prevalent median droplet size should be between about 30 and about 100 μm. If the droplets are too large (e.g., greater than about 120 μm), deposition takes place mainly in the anterior parts of the nose, and if the droplets are too small (e.g., less than about 10 μm), they can possibly be inhaled and reach the lungs, which should be avoided because of safety reasons.

Spray characterization (e.g., plume geometry, spray pattern, pump delivery, droplet size distribution (DSD)) of the delivered plume subsequent to spraying may be measured under specified experimental and instrumental conditions by appropriate and validated and/or calibrated analytical procedures known in the art. These include photography, laser diffraction, and impaction systems (cascade impaction, next generation impaction (NGI), etc.). Droplet size distribution can be controlled in terms of ranges for the D10, D50, D90, span [D90-D10)/050], and percentage of droplets less than 10 μm. In certain embodiments, a spray of a pharmaceutical composition described herein released from a device described herein will have a narrow DSD. The particle diameter "(D)" designations refer to the representative diameter where 10% (D10), 50% (D50) and 90% (D90) of the total volume of the liquid sprayed is made up of droplets with diameters smaller than or equal to the stated value.

A device configured for intranasal configuration described herein can administer a pharmaceutical composition described herein in the form of a spray with certain spray pattern characteristics. In some embodiments, the Dv90 of the spray of droplets is from about 40 μm to about 80 μm. In some embodiments, the Dv90 of the spray of droplets is from about 60 μm to about 80 μm. In some embodiments, the Dv90 of the droplets is from about 60 μm to about 70 μm. In some embodiments, the Dv50 of the droplets is from about 20 μm to about 40 μm. In some embodiments, the Dv50 of the droplets is from about 30 μm to about 40 μm. In some embodiments, the Dv50 of the droplets is from about 30 μm. In some embodiments, the Dv10 of the droplets is from about 10 μm to about 20 μm. In some embodiments, the Dv10 of the droplets is from about 12 μm to about 20 μm. In some embodiments, the Dv10 of the droplets is from about 10 μm to about 17 μm. In In some embodiments, the percent volume of droplets less than 10 μm is less than about 12%. In some embodiments, the percent volume of droplets less than 10 μm is less than about 10%. In some embodiments, the percent volume of droplets less than 10 μm is about 6.7%. In some embodiments, the percent volume of droplets less than 10 μm is about 6.3%. In some embodiments, the device sprays a spray pattern with a Dmax of about 50 mm. In some embodiments, the device sprays a spray pattern with a Dmax of about 40.2 mm. In some embodiments, the device sprays a spray pattern with a Dmax of about 40.7 mm. In some embodiments, the device sprays a spray pattern with an area of about 750 $mm^2$ to about 1500 $mm^2$. In some embodiments, the device sprays a spray pattern with an area of about 1100 $mm^2$. In some embodiments, the device sprays a spray pattern with an area of about 1110 $mm^2$. In some embodiments, the device sprays a spray pattern with an ovality ratio of about 1.0 to about 2.5. In some embodiments, the device sprays a spray pattern with an ovality ratio of about 1.0 to about 2.0. In some embodiments, the device sprays a spray pattern with an ovality ratio of about 1.2 to about 1.4.

In certain embodiments, the percent of droplets less than 10 μm is less than 12%. In certain embodiments, the percent of droplets less than 10 μm is less than 10%. In certain embodiments, the percent of droplets less than 10 μm is less than 5%. In certain embodiments, the percent of droplets less than 10 μm is less than 2%. In certain embodiments, the percent of droplets less than 10 μm is less than 1%.

Kits

Also provided are kits comprising a pharmaceutical composition or device described herein and written instructions for using the device. Also provided are kits comprising a device described herein and an opioid receptor antagonist. In some embodiments the kit further comprises written instructions. The written instructions provided herein can be instructions for use in treating a patient suffering from an opioid overdose or hydrate thereof. In some embodiments, the written instructions comprise instructions for administering a dose of a pharmaceutical composition described herein from a device described herein. The instructions can be written for comprehension both by a trained individual (e.g., a physician, nurse, nurse practitioner, or other professional trained in administering the dose from a device described herein) or untrained individual. In some embodiments, the written instructions comprise graphical illustrations of steps for administering the dose.

Autoclaving Processes

The pharmaceutical compositions and devices described herein can be sterilized in preparation for delivery to a patient in need thereof. Such sterilization can be accomplished using autoclaving techniques in which a container is filled with the composition under high-quality environmental conditions, such as those required by the aseptic filling techniques additionally described herein. Said high-quality environmental conditions can include high-quality aerobic conditions. Once such high-quality environmental conditions are achieved, the compositions are subjected to elevated temperatures through one or more cycles. In some embodiments, the container is a component of a device to be used to administer the composition to a patient suffering from a drug overdose or symptom thereof.

In one embodiment, provided herein is a process comprising the steps of: a. deoxygenating the pharmaceutical composition by sparging with nitrogen until the dissolved oxygen is NMT 1 ppm; b. filling a unit dose container with the pharmaceutical composition; c. removing oxygen from the head space gas of the unit dose container to provide a reduced oxygen head space unit dose container, then stoppering the unit dose container; and d. heating the deoxygenated unit dose container at a temperature of not more than 125° C.; thereby reducing bioburden of the pharmaceutical composition.

In one embodiment, provided herein is a process comprising the steps of: a. filling a unit dose container with the pharmaceutical composition; b. deoxygenating the unit dose container to provide a deoxygenated unit dose container; and c. heating the deoxygenated unit dose container at a temperature of not more than 125° C.; thereby sterilizing the pharmaceutical composition.

In embodiments of the described processes, the headspace of the deoxygenated unit dose container typically comprises not more than 15% oxygen, (e.g., not more than 10% oxygen, not more than 5% oxygen, not more than 1% oxygen, or not more than 0.01% oxygen).

Furthermore, heating the deoxygenated unit dose container can comprise subjecting the deoxygenated unit dose container to multiple heating cycles each lasting for about 5 minutes to about 1 hour. In some embodiments, heating the deoxygenated unit dose container comprises subjecting the deoxygenated unit dose container to three heating cycles each lasting for about 30 minutes. Exemplary temperatures of each heating cycle can be set to a temperature from about 100° C. to about 125° C.

Methods of Treatment

Also provided are methods of treating opioid overdoses and symptoms thereof and methods of using the devices and pharmaceutical compositions described herein for the same. In one embodiment, provided herein is a method of treating an opioid overdose or symptom thereof in a patient in need thereof, comprising administering to the patient the pharmaceutical composition described herein. In some embodiments, the pharmaceutical composition is administered to the patient from a device described herein.

Naloxone prevents or reverses the effects of opioids including respiratory depression, sedation and hypotension. Also, it can reverse the psychotomimetic and dysphoric effects of agonist-antagonists such as pentazocine. Naloxone causes abrupt reversal of narcotic depression which may result in nausea, vomiting, sweating, tachycardia, increased blood pressure, tremulousness, seizures and cardiac arrest, however, there is no clinical experience with naloxone hydrochloride overdosage in humans. In the mouse and rat the intravenous $LD_{50}$ is 150±5 mg/kg and 109±4 mg/kg respectively. In acute subcutaneous toxicity studies in newborn rats the $LD_{50}$ (95% CL) is 260 (228-296) mg/kg. Subcutaneous injection of 100 mg/kg/day in rats for 3 weeks produced only transient salivation and partial ptosis following injection: no toxic effects were seen at 10 mg/kg/day for 3 weeks.

Naloxone hydrochloride injection is indicated for the complete or partial reversal of narcotic depression, including respiratory depression, induced by opioids selected from: natural and synthetic narcotics, propoxyphene, methadone, and certain narcotic-antagonist analgesics: nalbuphine, pentazocine and butorphanol. Naloxone hydrochloride is also indicated for the diagnosis of suspected acute opioid over dosage. For the treatment of known or suspected narcotic overdose in adults an initial dose of 0.4 mg to 2 mg of naloxone hydrochloride intravenously is indicated. If the desired degree of counteraction and improvement in respiratory functions is not obtained, administration may be repeated at 2 to 3 minute intervals. If no response is observed after 10 mg of naloxone hydrochloride have been administered, the diagnosis of narcotic-induced or partial narcotic-induced toxicity should be questioned. The usual initial dose in children is 0.01 mg/kg body weight given IV. If this dose does not result in the desired degree of clinical improvement, a subsequent dose of 0.1 mg/kg body weight may be administered. When using naloxone hydrochloride injection in neonates a product containing 0.02 mg/mL should be used.

It has also been reported that naloxone hydrochloride is an effective agent for the reversal of the cardiovascular and respiratory depression associated with narcotic and possibly some non-narcotic overdoses. The authors stated that due to naloxone's pharmacokinetic profile, a continuous infusion protocol is recommended when prolonged narcotic antagonist effects are required. (Handal et al., Ann Emerg Med. 1983 July; 12(7):438-45).

In one embodiment of the present disclosure, provided herein are methods of treating an opioid overdose or symptoms thereof in patient in need thereof, comprising administering to the patient a pharmaceutical composition described herein or unit dose described herein. In some embodiments, the patient exhibits one or more symptoms selected from the group consisting of respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing; erratic or stopped pulse, choking or gurgling sounds, blue or purple fingernails or lips, slack or limp muscle tone, contracted pupils, and vomiting. In some embodiments, the patient exhibits respiratory depression. In some embodiments, the opioid overdose or symptom thereof is caused by an opioid selected from the group consisting of codeine, morphine, methadone, fentanyl, carfentanyl, acetyl fentanyl, oxycodone hydrochloride, hydrocodone bitartrate, hydromorphone, oxymorphone, meperidine, propoxyphene, opium, heroin, tramadol, tapentadol, and a narcotic-antagonist analgesic. In some embodiments, the narcotic-antagonist analgesic is selected from the group consisting of nalbuphine, pentazocine, and butorphanol.

In some embodiments, the patient is a mammal In some embodiments, the patient is a human. In some embodiments, the patient is an opioid overdose patient or a suspected opioid overdose patient.

The patient may be in a lying, supine, or recovery position during the course of the described methods. In some embodiments, said patient is in a lying position while being administered the pharmaceutical composition or the unit dose. In some embodiments, said patient is in a supine position. In some embodiments, said patient is in a recovery position.

In some embodiments, said therapeutically effective amount of an opioid receptor antagonist is delivered by an untrained individual.

In some embodiments, the opioid overdose or symptom thereof is caused by a fentanyl derivative of Formula (I)

(I)

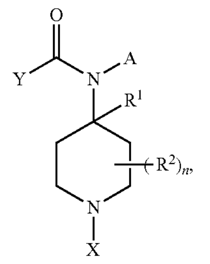

wherein A is aryl or heteroaryl optionally substituted with halo, $C_1$-$C_3$ alkyl, or $C_1$-$C_3$ alkoxy, X is $C_1$-$C_3$ alkyl or hydroxyethyl, optionally substituted with —$COOCH_3$, aryl, or heteroaryl optionally substituted with both $C_1$-$C_3$ alkyl and =O, Y is $C_1$-$C_4$ alkyl, $C_2$-$C_3$ alkenyl, $C_1$-$C_3$ alkoxy, $C_1$-$C_3$ alkoxyalkyl, cycloalkyl, or heteroaryl, R1 and R2 are each independently selected from the group consisting of phenyl, $C_1$-$C_3$ alkyl, $C_2$-$C_3$ alkenyl, $C_1$-$C_3$ alkoxyalkyl, or $C_1$-$C_3$ alkoxy, and —$COOCH_3$, and n is 1, 2, or 3.

In some embodiments, the pharmaceutical composition used in the methods described herein comprises a therapeutically effective amount of naloxone hydrochloride or a hydrate thereof. In some embodiments, the hydrate of naloxone hydrochloride is naloxone hydrochloride dihydrate. In some embodiments, the therapeutically effective amount is equivalent to about 2 mg to about 16 mg of naloxone hydrochloride per 0.1 mL of composition. In some embodiments, the therapeutically effective amount is equivalent to about 8 mg to about 12 mg of naloxone hydrochloride per 0.08 mL to 0.12 mL of composition. In some embodiments, the therapeutically effective amount is equivalent to about 8 mg to about 11 mg of naloxone hydrochloride per 0.1 mL or 0.11 mL of composition. In some embodiments, the therapeutically effective amount is equivalent to about 8 mg to about 10 mg of naloxone hydrochloride per 0.1 mL or 0.11 mL of composition. In some embodiments, the therapeutically effective amount is equivalent to about 10 mg of naloxone hydrochloride per 0.11 mL of composition. In some embodiments, the therapeutically effective amount is equivalent to about 9 mg of naloxone hydrochloride per 0.1 mL of composition.

In some embodiments, upon nasal delivery of said pharmaceutical composition to said patient, less than about 20% of said pharmaceutical composition leaves the nasal cavity via drainage into the nasopharynx or externally. In some embodiments, the upon nasal delivery of said pharmaceutical composition to said patient, less than about 10% of said pharmaceutical composition leaves the nasal cavity via drainage into the nasopharynx or externally. In some embodiments, the upon nasal delivery of said pharmaceutical composition to said patient, less than about 5% of said pharmaceutical composition leaves the nasal cavity via drainage into the nasopharynx or externally.

In some embodiments, the plasma concentration versus time curve of an opioid receptor antagonist administered in said patient has a $T_{max}$ of between about 20 and about 60 minutes. In some embodiments, the plasma concentration versus time curve of an opioid receptor antagonist administered in said patient has a $T_{max}$ of less than 55 minutes. In some embodiments, an opioid receptor antagonist administered in said patient has a $T_{max}$ of less than 50 minutes. In some embodiments, an opioid receptor antagonist administered in said patient has a $T_{max}$ of about 45 minutes.

In some embodiments, the administration yields a mean naloxone plasma concentration of ≥0.2 ng/mL within 2.5 minutes in said patient. In some embodiments, the administration yields a mean naloxone plasma concentration of ≥1 ng/mL within 5 minutes in said patient. In some embodiments, the administration yields a mean naloxone plasma concentration of ≥3 ng/mL within 10 minutes in said patient.

In some embodiments, the pharmaceutical composition is sufficient to provide a $t_{max}$ of about 0.75 h to about 1 h in the patient. In some embodiments, the unit dose is sufficient to provide a $t_{max}$ of about 0.75 h to about 1 h in the patient. In some embodiments, the pharmaceutical composition is sufficient to provide a $C_{max}$ of about 9 ng/mL to about 10 ng/mL in the patient. In some embodiments, unit dose is sufficient to provide a $C_{max}$ of about 9 ng/mL to about 10 ng/mL in the patient. In some embodiments, the pharmaceutical composition is sufficient to provide an $AUC_{(0-8)}$ of about 19 h·ng/mL to about 20 h·ng/mL in the patient. In some embodiments, the unit dose is sufficient to provide an $AUC_{(0-8)}$ of about 19 h·ng/mL to about 20 h·ng/mL in the patient. In some embodiments, the pharmaceutical composition is sufficient to provide an $AUC_{(0-\infty)}$ of about 19 h·ng/mL to about 20 h·ng/mL in the patient. In some embodiments, the unit dose is sufficient to provide an $AUC_{(0-\infty)}$ of about 19 h·ng/mL to about 20 h·ng/mL in the patient. In some embodiments, the pharmaceutical composition is sufficient to provide a $t_{1/2}$ of about 1 h to about 2 h in the patient. In some embodiments, the unit dose is sufficient to provide a $t_{1/2}$ of about 1 h to about 2 h in the patient.

Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "active ingredient" or "pharmaceutically active compound" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The term "actuation," as used herein, refers to the operation of a device described herein such that a pharmaceutical composition described herein or unit dose thereof is delivered therefrom.

The term "agonist," as used herein, refers to as used herein refers to a moiety that interacts with and activates a receptor, and thereby initiates a physiological or pharmacological response characteristic of that receptor.

The term "antagonist," as used herein, refers to a moiety that competitively binds to a receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

As used herein, the term "autoclave" refers to a device that can be used for autoclave sterilization or bioburden reduction. The term "autoclave sterilization" refers to any autoclave sterilization process, including, for example and without limitation, and steam autoclave processes. In exemplary aspects, the "autoclave sterilization" process can use high-pressure saturated steam and occur at a temperature over 100° C. and over a time period about 10 to about 60 minutes.

The term "AUC," as used herein, refers to the area under the drug plasma concentration-time curve.

The term "$AUC_{0-t}$," as used herein, refers to the area under the drug plasma concentration-time curve from t=0 to the last measurable concentration.

The term "$AUC_{0-\infty}$," as used herein, refers to the area under the drug plasma concentration-time curve extrapolated to ∞.

As used herein, the term "aqueous solution" refers to a composition comprising in whole, or in part, water.

The term "bioavailability (F)," as used herein, refers to the fraction of a dose of drug that is absorbed from its site of administration and reaches, in an unchanged form, the systemic circulation.

The term "absolute bioavailability" is used when the fraction of absorbed drug is related to its IV bioavailability. It may be calculated using the following formula:

$$F = \frac{AUC_{extravascular}}{AUC_{intravenous}} \times \frac{\text{Dose}_{intravenous}}{\text{Does}_{extravascular}}$$

The relative bioavailability ($F_{rel}$) is used to compare two different extravascular routes of drug administration and it may be calculated using the following formula:

$$F_{rel} = \frac{AUC_{extravascular1}}{AUC_{extravascular2}} \times \frac{\text{Dose}_{extravascular2}}{\text{Does}_{extravascular1}}$$

As used herein, the terms "buffer," "buffer system," or "buffering component" refers to a compound that, usually in combination with at least one other compound, provides a chemical system in solution that exhibits buffering capacity, that is, the capacity to neutralize, within limits, the pH lowering or raising effects of either strong acids or bases (alkali), respectively, with relatively little or no change in the original pH (e.g., the pH before being affected by, e.g., strong acid or base). For example, a buffer described herein maintains or controls the pH of a solution to a certain pH range. For example, "buffering capacity" can refer to the millimoles (mM) of strong acid or base (or respectively, hydrogen or hydroxide ions) required to change the pH by one unit when added to one liter (a standard unit) of the buffer solution. From this definition, it is apparent that the smaller the pH change in a solution caused by the addition of a specified quantity of acid or alkali, the greater the buffer capacity of the solution. See, for example, Remington: The Science and Practice of Pharmacy, Mack Publishing Co., Easton, Pennsylvania ($19^{th}$ Edition, 1995), Chapter 17, pages 225-227. The buffer capacity will depend on the kind and concentration of the buffer components.

The term "clearance (CL)," as used herein, refers to the rate at which a drug is eliminated divided by its plasma concentration, giving a volume of plasma from which drug is completely removed per unit of time. CL is equal to the elimination rate constant (λ) multiplied by the volume of distribution ($V_d$), wherein "$V_d$" is the fluid volume that would be required to contain the amount of drug present in the body at the same concentration as in the plasma.

The term "apparent clearance (CL/F)," as used herein, refers to clearance that does not take into account the bioavailability of the drug. It is the ratio of the dose over the AUC.

The term "$C_{max}$," as used herein, refers to the maximum observed plasma concentration.

The term "confidence interval," as used herein, refers to a range of values which will include the true average value of a parameter a specified percentage of the time.

The term "device," as used herein, refers to an apparatus capable of delivering a drug product (e.g., a pharmaceutical composition described herein or a unit dose described herein) to a patient. In some embodiments, the device is used to deliver a drug to a patient in need thereof.

The term "delivery time," as used herein, refers to the amount of time that elapses between a determination made by a healthcare professional, or an untrained individual that an individual is in need of nasal delivery of an opioid receptor antagonist and completion of the delivery.

The term "elimination rate constant (λ)," as used herein, refers to the fractional rate of drug removal from the body. This rate is constant in first-order kinetics and is independent of drug concentration in the body. λ is the slope of the plasma concentration-time line (on a logarithmic y scale).

The term "equivalent," as used herein refers to a weight of an opioid receptor antagonist selected from naloxone and pharmaceutically acceptable salts thereof that is equimolar to a specified weight of naloxone hydrochloride. For example, 8 mg of anhydrous naloxone hydrochloride (molecular weight, 363.84) is equivalent to about 7.2 mg of naloxone freebase (molecular weight, 327.37), and to about 8.8 mg of naloxone hydrochloride dihydrate (molecular weight 399.87).

The term "filled," as used herein, refers to an association between a device and a pharmaceutical composition, for example, when a pharmaceutical composition described herein comprising a therapeutically effective amount of an opioid receptor antagonist is present within a reservoir that forms a part of a device described herein.

The term "hydrate," as used herein, refers to an opioid receptor antagonist described herein or a salt thereof that further includes a stoichiometric or non-stoichiometric amount of water bound by non-covalent intermolecular forces.

The term "in need of treatment" and the term "in need thereof" when referring to treatment are used interchangeably herein and refer to a judgment made by a caregiver (e.g. physician, nurse, or nurse practitioner) that a patient will benefit from treatment.

As used herein, "spray pattern" is the shape of the plume when looking downward on the nasal spray unit as the product is emitted from the nasal spray unit.

As used herein, "ovality" or "ovality ratio" is the ratio of Dmax/Dmin, where Dmax and Dmin are the length of the longest and shortest line, respectively, that passes through the weighted center of mass drawn within the parameter of the spray pattern. In some embodiments, Dmax and Dmin are in units of mm.

The term "glycerin" refers to the compound propane-1,2,3-triol, which has the structure:

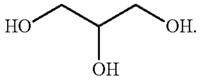

The term "naloxone," as used herein, refers to a compound of the following structure:

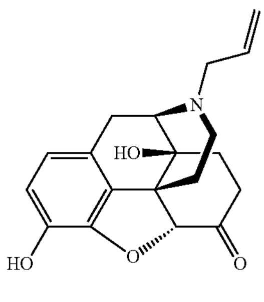

The CAS registry number for naloxone is 465-65-6. Other names for naloxone include: 17-allyl-4,5a-epoxy-3,14-dihydroxymorphinan-6-one; (-)-17-allyl-4,5a-epoxy-3,14-dihydroxymorphinan-6-one; 4,5a-epoxy-3,14-dihydroxy-17-(2-propenyl)morphinan-6-one; and (-)-12-allyl-7,7a,8,9-tetrahydro-3,7a-dihydroxy-4aH-8,9c-iminoethanophenanthro[4,5-bcd]furan-5(6H)-one. Naloxone can be provided as a pharmaceutically acceptable salt, hydrate, or solvate thereof. For example, naloxone hydrochloride may be anhydrous (CAS Reg. No. 357-08-4) and also forms a dihydrate (CAS No. 51481-60-8). It has been sold under various brand names including NARCAN™, NALONE™, NALOSSONE™, NALOXONA™, NALOXONUM™, NARCANTI™, and NARCON™.

The term "naltrexone," as used herein, refers to a compound of the following structure:

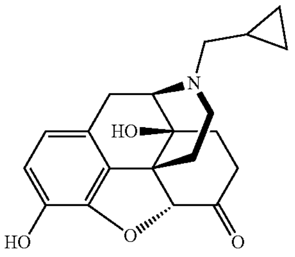

or a pharmaceutically acceptable salt, hydrate, or solvate thereof. The CAS registry number for naltrexone is 16590-41-3. Other names for naltrexone include: 17-(cyclopropylmethyl)-4,5a-epoxy-3,14-dihydroxymorphinan-6-one; (5a)-17-(cyclopropylmethyl)-3,14-dihydroxy-4,5-epoxymorphinan-6-one; and (1S,5R,13R,17S)-4-(cyclopropylmethyl)-10,17-dihydroxy-12-oxa-4-azapentacy-clo[9.6.1.01,13.05,17.07,18]octadeca-7(18),8,10-trien-14-one. Naltrexone hydrochloride (CAS Reg. No. 16676-29-2) has been marketed under the trade names ANTAXONE™, DEPADE™, NALOREX™, REVIA™, TREXANr™, VIVITREX™, and VIVITROL™.

The term "methylnaltrexone," as used herein, refers to a pharmaceutically acceptable salt comprising the cation (5a)-17-(cyclopropylmethyl)-3,14-dihydroxy-17-methyl-4,5-epoxymorphinaniu-m-17-ium-6-one a compound of the following structure:

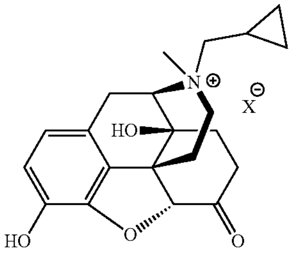

wherein $X^{\ominus}$ is a pharmaceutically acceptable anion. Methylnaltrexone bromide (CAS Reg. No. 75232-52-7) has been marketed under the trade name RELISTOR™.

The term "nalmefene," as used herein, refers to 17-cyclopropylmethyl-4,5a-epoxy-6-methylenemorphinan-3,14-diol, a compound of the following structure:

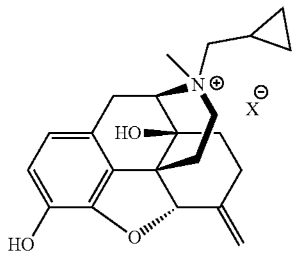

Nalmefene hydrochloride (CAS Reg. No. 58895-64-0) has been marketed under the trade names NALMETRENE™, CERVENE™, REVEX™, ARTHRENE™, and INCYSTENE™.

"Chlorobutanol" as used herein refers to the compound having the structure

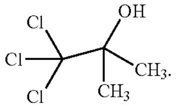

Chlorobutanol as defined herein (1,1,1-trichloro-2-methylpropan-2-ol; CAS Reg. No. 57-15-8) is a known preservative that can be used as an antibacterial and/or antifungal agent in pharmaceutical and cosmetic formulations. In an embodiment, the chlorobutanol is anhydrous. In another embodiment, the chlorobutanol is a solvate, e.g., a hydrate such as a hemihydrate.

"Benzyl alcohol" as used herein refers to the compound having the structure

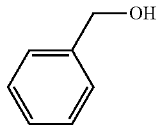

Benzyl alcohol as defined herein (phenylmethanol; CAS Reg. No. 100-51-6) is a known preservative that can be used as a bacteriostatic preservative in pharmaceutical, food, and cosmetic formulations. In an embodiment, the benzyl alcohol is anhydrous. In another embodiment, the benzyl alcohol is a salt, e.g., a sodium salt of benzyl alcohol such as sodium benzoate.

The term "nostril," as used herein, is synonymous with "naris."

"Intranasal administration," and "nasal delivery" are used interchangeably herein.

The term "opioid receptor antagonist" includes, in addition to naloxone and pharmaceutically acceptable salts thereof: naltrexone, methylnaltrexone, and nalmefene, and pharmaceutically acceptable salts thereof. In some embodiments, the opioid receptor antagonist is naloxone hydrochloride. In some embodiments, the opioid receptor antagonist is naloxone hydrochloride dihydrate. In some embodiments, the opioid receptor antagonist is naltrexone hydrochloride. In some embodiments, the opioid receptor antagonist is methylnaltrexone bromide. In some embodiments, the opioid receptor antagonist is nalmefene hydrochloride. In some embodiments, the nasally administering is accomplished using a device described herein.

The term "opioid overdose," as used herein, refers to an acute medical condition induced by excessive use of one or more opioids. Symptoms of opioid overdose include respiratory depression (including postoperative opioid respiratory depression, acute lung injury, and aspiration pneumonia), central nervous system depression (which may include sedation, altered level consciousness, miotic (constricted) pupils), and cardiovascular depression (which may include hypoxemia and hypotension). Visible signs of opioid overdose or suspected opioid overdose include: unresponsiveness and/or loss of consciousness (won't respond to stimuli such as shouting, shaking, or rubbing knuckles on sternum); slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose and/or quantify, particularly by a lay person, as used herein, treatment of opioid overdose is meant to include treatment of suspected opioid overdose in opioid-intoxicated patients. Opioids that may induce overdose include, codeine, morphine, methadone, fentanyl, oxycodone HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol. In some embodiments, the opioid is provided in a tamper-proof formulation. In some embodiments, the opioid provided is in a tamper-resistant formulation. In some embodiments, the opioid is provided from ACUROX™, Oxycodone DETERx™, Egalet hydrocodone, Egalet morphine, Egalet oxycodone, EXALGO™, OPANA™, or REMOXY™.

The term "osmolality," as used herein, refers to a measure of number of dissolved particles in a fluid expressed as mOsm/kg water.

As used herein, "particulate matter" refers to any matter that is insoluble or partially soluble in water or an aqueous mixture. In some embodiments, the particulate matter comprises visible particles. "Particulate matter" also encompasses other particulates such as lint, glass, metal, and the like. In an embodiments, particulate matter encompasses subvisible particles (e.g., less than 100 μm in diameter).

The term "patient," as used herein, refers to any subject (preferably human) afflicted with a condition likely to benefit from a treatment with a therapeutically effective amount of an opioid receptor antagonist.

The term "pharmaceutical composition," as used herein, refers to a composition comprising at least one active ingredient; including but not limited to, salts, solvates and hydrates of the opioid receptor antagonists described herein, whereby the composition is amenable to use for a specified, efficacious outcome in a mammal (for example, without limitation, a human).

The term "prone," as used herein, refers to a patient who is lying face down.

The term "preservative," as used herein, refers to a substance (e.g., a chemical compound including salts) that may be added to products (e.g., pharmaceutical compositions described herein) to provide antimicrobial activity and to prevent proliferation of microorganisms.

The term "recovery position," as used herein, means a position of the human body in which a patient lies on his/her side, with a leg or knee out in front (e.g., to prevent rolling onto his/her stomach) and at least one hand supporting the head (e.g., to elevate the face to facilitate breathing and prevent inhalation of vomit).

The term "solvate," as used herein, refers to an opioid receptor antagonist described herein or a salt thereof, that further includes a stoichiometric or non-stoichiometric amount of a solvent bound by non-covalent intermolecular forces. Preferred solvents are volatile, non-toxic, and/or acceptable for administration to humans in trace amounts. A "hydrate" as used herein refers to an opioid receptor antagonist described herein or a salt thereof, that further includes a stoichiometric or non-stoichiometric amount of water bound by non-covalent intermolecular forces.

The term "aseptic filling," as used herein, refers methods of manufacturing the devices and pharmaceutical compositions described herein, such that the use of preservatives is not required. Sterile drug products may be produced using aseptic processing or terminal sterilization. Terminal sterilization usually involves filling and sealing product containers under high-quality environmental conditions. In an aseptic process, the drug product, container, and closure are first subjected to sterilization methods separately, as appropriate, and then brought together.

As used herein, "sterilized" means essentially free or free of microorganisms (e.g., bacteria, viruses, fungi, etc.) and their spores. Often sterility assurances of a $1\times10^6$ reduction are required to claim terminal sterility. In various embodiments the compositions are sterilized by heat treatment, such as steam sterilization or autoclaving, which can include the techniques described herein. In some embodiments, heat treatment, regardless of temperature, time or type, which results in a $1\times10^6$ sterility assurance level (the probability that a given unit is not sterile is one in a million) is used. In some embodiments the compositions have zero bioburden following autoclaving. As used herein, "sterilizing" refers to the action taken to obtain a sterilized or zero bioburden composition.

The term "storage-stable," as used herein, refers to a pharmaceutical composition in which at least 90%, (e.g., at least 99%, 90% to 110%, or 95% to 99.5%) of the active ingredient remains in an undegraded state after storage of the pharmaceutical composition at specified temperature and humidity for a specified time, for example, for 12 months at 25° C. and 60% relative humidity.

The term "supine," as used herein, refers to a patient who is lying face up.

As used herein, "substantially free" means that the pharmaceutical compositions or unit doses described herein comprise a preservative or particulate matter each in an amount of no more than 2% by weight based on the total weight of the composition. In some embodiments, a composition described herein comprises the preservative in no more than 2% by weight, no more than 1.5% by weight, no more than 1% by weight, no more than 0.5% by weight, no more than 0.1% by weight, no more than 0.01% by weight, no more than 0.001% by weight, or no more than 0.0001% by weight. In some embodiments, a composition described herein comprises the particulate matter in no more than 2% by weight, no more than 1.5% by weight, no more than 1% by weight, no more than 0.5% by weight, no more than 0.1% by weight, no more than 0.01% by weight, no more than 0.001% by weight, or no more than 0.0001% by weight. In some embodiments, a composition described herein comprises 0% of the preservative. In some embodiments, a composition described herein comprises no particulate matter.

The term "$t_{1/2}$" or "half-life," as used herein, refers to the amount of time required for half of a drug to be eliminated from the body or the time required for a drug concentration to decline by half.

The term "therapeutically effective amount," as used herein, refers to the amount of active compound or pharmaceutical agent that elicits the biological or medicinal response in a tissue, system, or individual that is being sought by a researcher, healthcare provider or individual.

The term "tonicity agent," as used herein, refers to a compound which modifies the osmolality of a formulation, for example, to render it isotonic. Tonicity agents include, dextrose, lactose, sodium chloride, calcium chloride, magnesium chloride, sorbitol, sucrose, mannitol, trehalose, raffinose, polyethylene glycol, hydroxyethyl starch, glycine and the like.

The term "tomography," as used herein, refers to a process of imaging by sections. The images may be looked at individually, as a series of two-dimensional slices or together, as a computer-generated three-dimensional representation.

The term "pH," as used herein, refers to a scale used to specify how acidic or basic a water-based solution is.

The term "pharmaceutically acceptable," as used herein, refers to a component of a pharmaceutical composition that it compatible with the other ingredients of the formulation and not overly deleterious to the recipient thereof.

The term "$T_{max}$" as used herein, refers to the time from administration of the pharmaceutical compositions described herein to maximum drug plasma concentration.

The term "untrained individual" refers to an individual administering to patient an opioid receptor antagonist using a device described herein, wherein the individual is not a healthcare professional and has received no training in the use of the device, such as through an overdose education and nasal naloxone distribution (OEND) program.

As used herein, a "unit dose" is a discrete amount of a pharmaceutical composition described herein comprising a predetermined amount of the active ingredient. The amount of the active ingredient is generally equal to the dosage of the active ingredient which would be administered to a patient and/or a convenient fraction of such a dosage such as, for example, one-half or one-third of such a dosage.

Examples of unit doses described herein where naloxone hydrochloride is the active ingredient include but are not limited to doses of pharmaceutical compositions comprising: 4 mg of naloxone hydrochloride per 100 μL of pharmaceutical composition, 4 mg of naloxone hydrochloride per 110 μL of pharmaceutical composition, 6 mg of naloxone hydrochloride per 100 μL of pharmaceutical composition, 6 mg of naloxone hydrochloride per 110 μL of pharmaceutical composition, 7 mg of naloxone hydrochloride per 100 μL of pharmaceutical composition, 7 mg of naloxone hydrochloride per 110 μL of pharmaceutical composition, 8 mg of naloxone hydrochloride per 100 μL, of pharmaceutical composition, 8 mg of naloxone hydrochloride per 110 μL of pharmaceutical composition, 9 mg of naloxone hydrochloride per 100 μL of pharmaceutical composition, 9 mg of naloxone hydrochloride per 110 μL of pharmaceutical composition, 10 mg of naloxone hydrochloride per 100 μL of pharmaceutical composition, 10 mg of naloxone hydrochloride per 110 μL of pharmaceutical composition, 11 mg of naloxone hydrochloride per 100 μL of pharmaceutical composition, 11 mg of naloxone hydrochloride per 110 μL of pharmaceutical composition, 12 mg of naloxone hydrochloride per 100 μL of pharmaceutical composition, and 12 mg of naloxone hydrochloride per 110 μL of pharmaceutical composition.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $—CH_3$). In certain embodiments, the alkyl group is substituted $C_{1-10}$ alkyl. Common alkyl abbreviations include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$), or i-Bu ($—CH_2CH(CH_3)_2$).

"Alkoxy" refers to the group $—OR^{AB}$ where $R^{AB}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

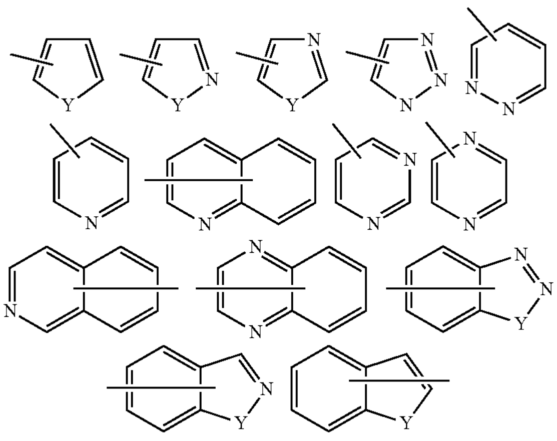

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "Cycloalkyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

Alkyl, alkoxyalkyl, carbocyclyl, cycloalkyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Further, to the extent that the method does not rely on the particular order of steps set forth herein, the particular order of the steps should not be construed as limitation on the claims. The claims directed to the methods described herein should not be limited to the performance of their steps in the order written, and one skilled in the art can readily appreciate that the steps may be varied and still remain within the spirit and scope of the present invention.

EXAMPLES

In order that the invention described herein may be more fully understood, the following examples are set forth. The examples described in this application are offered to illustrate the aspects of the invention and their embodiments provided herein and are not to be construed in any way as limiting their scope.

Abbreviations

| | |
|---|---|
| API | active pharmaceutical ingredient |
| AR | as required |
| AUC | area under the curve |
| $D_{max}$ | maximum diameter |
| EDTA | ethylenediaminietetraacetic acid |
| HPLC | high-performance liquid chromatography |
| NF | national formulary and drug standards laboratory |
| NMT | no more than |
| NX | naloxone hydrochloride dihydrate |
| PSIA | pounds per square inch absolute |
| Q.S. | quantity sufficient (to make) |
| RRT | relative retention time |
| RT | retention time |
| SCU | spray content uniformity |
| TAMC | total aerobic microbial count |
| TSA | tryptic soy agar |
| TSB | tryptic soy broth |
| USP | United States pharmacopeia |
| UV | ultraviolet |

Methods of Preparation and Characterization

The aqueous pharmaceutical compositions of the present disclosure may be better understood in connection with the following methods which illustrate a means by which the compositions can be prepared and characterized. The aqueous pharmaceutical compositions of the present disclosure can be prepared and characterization by a variety of procedures. As described herein, the aqueous pharmaceutical compositions may be formulations. Representative procedures are shown, but not limited to, below.

1. Formulation Preparation:

Exemplary formulations described herein was prepared using the following procedure: In a container, the excipients, glycerin or additional viscosity modifiers and trisodium citrate dihydrate were added to USP Purified Water and stirred. Once the excipients were dissolved, Naloxone HCl Dihydrate was slowly added and the solution volume was increased to approximately 90% of the final batch volume to allow API dissolution. A final pH target was achieved by adjusting either down with hydrochloric acid or up with sodium hydroxide, as necessary. The solution was transferred to a volumetric flask and filled to volume with USP Purified Water to reach the volume corresponding to the batch size.

2. Exemplary Method of Autoclave Sterilization/Terminal Autoclaving for Bioburden Reduction:

Formulated bulk drug products prepared as described above (see for example, Examples 1, 2, and 3 below) were sparged with nitrogen until the dissolved oxygen concentration was NMT 1 ppm. Sparged bulk drug products were then filtered and filled into unit dose vials. A nitrogen blanket was applied during filling. The unit dose vials were stoppered such that the oxygen concentration in the headspace of the vial was less than 15%. The filled and stoppered vials were then autoclaved as summarized below:

Filled and stoppered unit dose vials prepared as described in the preceding paragraph were then placed in an autoclave chamber. The autoclave chamber was then purged with clean steam and subjected to vacuum. The chamber was then subjected to three cycles, each at 30 seconds, in which the chamber was charged with clean steam and then subjected to vacuum. The chamber was then charged with clean steam to achieve a pressure of no more than 32.0 PSIA and set at a temperature of not more than 125° C. The unit dose vials were autoclaved under these conditions for not more than 60 minutes. The chamber was cooled. The pressure in the chamber was then reduced to atmospheric pressure. The chamber was then back-filled with air and the vial was removed.

3. HPLC Assay

In some examples, the below formulations were evaluated using an assay described herein. The assay consists of a modified European Pharmacopoeia monograph related substances method for Naloxone. An end-capped octysilyl silica gel 5-μm HPLC column (4.6 mm×150 mm) was maintained at 40° C. The mobile phase gradient started with 100% mobile phase A (CH3CN:THF:buffer, 2:4:94) and ramped linearly to 100% mobile phase B (CH3CN:THF:buffer, 4:17:79) over 60 minutes with a 1.5 mL/min flow rate. A UV/Vis detector wavelength was set at 230 nm and a 10-μL injection volume was used.

4. Microbial Enumeration/Specified Microorganisms Quantification Methods

4a. Total Aerobic Microbial Count

The total aerobic microbial count in an exemplary formulation provided herein was measured using the following procedure: Total Aerobic Microbial Count (TAMC) was a procedure used to determine the number of microorganisms present in a drug product. The method follows United States Pharmacopeia (USP) Chapter <61> Microbiological Examination of Nonsterile Products: Microbial Enumeration Tests. The samples were sprayed into Tryptic Soy Broth (TSB), the entire contents of the sample preparation was filtered and plated onto TSA. Microbial colonies were enumerated (counted) on the agar plates after the incubation length of 3-5 days at 30-35° C. elapses.

4b. Total Yeasts and Molds Count

The total yeast and mold count in an exemplary formulation provided herein was measured using the following procedure: Total Yeasts and Molds Count (TAMC) was a procedure used to determine the number of fungi (yeasts and molds) present in a drug product. The methodology follows USP Chapter <61>. The samples were sprayed into TSB, the entire contents of the sample preparation was filtered and plated onto Sabouraud Dextrose Agar (SDA). Fungal colonies were enumerated (counted) on the agar plates after the incubation length of 5-7 days at 20-25° C. elapses.

5. Nasal Spray Characterization Methods

In some examples, nasal spray of the below exemplary formulations have been characterized using the procedures described herein. The properties evaluated using said characterization methods include pH, osmolality, spray pattern, and droplet size distribution.

5a. pH pH of the solution was measured by immersing a probe into the solution which was connected to a standard laboratory pH meter.

5b. Osmolality

Osmolality of the solution was determined by using an Advanced Instruments, Inc. osmometer equipped to measure osmolality by freezing point depression.

5c. Spray Pattern

The spray pattern of the spray was determined by the use of a PROVERIS SPRAYVIEW® system. To perform the testing, the nasal spray unit was positioned vertically. The tip of the nozzle of the nasal spray was positioned to be 30-40 mm from the laser beam of the SprayView system. The unit was automatically actuated using a Proveris Vereo automated actuator. The spray traveled through the laser and the spray pattern the droplet size distribution was determined.

5d. Droplet Size Distribution

The droplet size distribution of the spray was determined by the use of a Malvern SPRAYTEC® system. To perform the testing, the nasal spray unit was positioned vertically. The tip of the nozzle of the nasal spray was positioned to be 30-40 mm from the laser beam of the SPRAYTEC® system. The unit was automatically actuated using a Proveris Vereo NSx automated actuator. The spray travels through the laser and the droplet size distribution was determined.

6. Degradation Studies

In some examples, degradation of the below exemplary formulations can be evaluated using the following procedure: The assay consisted of a modified European Pharmacopoeia monograph related substances method for naloxone. An end-capped octysilyl silica gel 5-μm HPLC column (4.6 mm×150 mm) was maintained at 40° C. The mobile phase gradient started with 100% mobile phase A ($CH_3CN$:THF:buffer, 2:4:94) and ramped linearly to 100% mobile phase B ($CH_3CN$:THF:buffer, 4:17:79) over 60 minutes with a 1.5 mL/min flow rate. A UV/Vis detector wavelength was set at 230 nm and a 10-μL injection volume was used.

Example 1: Exemplary Formulation A-1

The below exemplary formulation was prepared and autoclaved based on the procedures described in the above Methods of Preparation and Characterization. The compositional makeup of the formulation is described in Table 1.

TABLE 1

| Ingredient | Quantity (mg/100 μL) | % w/w |
|---|---|---|
| Naloxone HCl Dihydrate | 10.99 | 10.52 |
| Trisodium Citrate Dihydrate | 0.30 | 0.28 |
| Glycerin | 1.4 | 1.34 |
| Propylene Glycol | 3.0 | 2.87 |
| NaOH or HCl to adjust pH | As required | As required |
| Purified Water | 88.8 | 84.99 |
| Total: | 104.5 | 100 |

Example 2: Exemplary Formulation A-2

The below exemplary formulation was prepared, autoclaved, and characterized based on the procedures described in the above Methods of Preparation and Characterization. The composition makeup of the formulation is described in Table 2a, exemplary properties are described in Table 2b, exemplary spray pattern properties are described in Tables 2c and 2d, and exemplary degradation properties are described in Table 2e.

TABLE 2a

Exemplary formulation A-2

| Component | Grade | Composition % w/w |
|---|---|---|
| Naloxone HCl Dihydrate (corresponding to naloxone HCl) | USP | 9.65 (8.78) |
| Glycerin | USP | 1.35 |
| Trisodium citrate Dihydrate | USP | 0.28 |
| Hydrochloric Acid | NF | AR |
| Sodium Hydroxide | NF | AR |
| Purified Water | USP | QS |
| Total: | | 100.00 |

Formulation A-2 was tested for aspect, HPLC, assay, pH and osmolality. The procedure used for the tests are described in the above Methods of Preparation and Characterization. Table 2b summarizes data for this formulation.

TABLE 2b

Exemplary properties of batches of formulation A-2

| Test | Batch 1 | Batch 2 | Batch 3 |
|---|---|---|---|
| Aspect | A clear, colorless solution free from visible particles. | A clear, colorless solution free from visible particles. | A clear, colorless solution free from visible particles. |
| Assay (HPLC) | 100% | 103% | 102% |
| pH | 4.3 | 4.3 | 4.3 |
| Osmolality | 558 mOsm/kg | 562 mOsm/kg | 561 mOsm/kg |

The net content, pump delivery, and SCU of a spray of formulation A-2 were evaluated. The procedure used for this evaluation is described in the above Methods of Preparation and Characterization. Table 2c summarizes data for this formulation.

TABLE 2c

Exemplary spray pattern properties of batches formulation A-2

| Test | Batch 1 | Batch 2 | Batch 3 |
|---|---|---|---|
| Net Content | Mean: 124.4% | Mean: 123.2% | Mean: 123.1% |
| Pump Delivery | Mean: 101% | Mean: 100% | Mean: 101% |
| Spray Content Uniformity (SCU) | Mean: 102% | Mean 102% | Mean: 102% |

The spray pattern, droplet size distribution, microbial enumeration/specified microorganisms of a spray of formulation A-2 were evaluated. The procedure used for this evaluation is described in the above Methods of Preparation and Characterization. Table 2d summarizes data for this formulation.

TABLE 2d

| Exemplary spray pattern properties of formulation A-2 | | | |
|---|---|---|---|
| Test | Batch 1 | Batch 2 | Batch 3 |
| Spray Pattern | | | |
| Shape | Conforms | Conforms | Conforms |
| Density | Conforms | Conforms | Conforms |
| $D_{max}$ | 38 mm | 46.5 mm | 35.5 mm |
| Ovality | 1.85 | 1.356 | 1.234 |
| Droplet Size Distribution | | | |
| $D_{10}$ | 14.74 μm | 13.77 μm | 13.21 μm |
| $D_{50}$ | 30.93 μm | 29.45 μm | 28.54 μm |
| $D_{90}$ | 68.42 μm | 63.68 μm | 61.70 μm |
| Span | 1.877 | 1.694 | 1.701 |
| % Volume < 10 μm | 1.731 | 3.132% | 4.104% |
| Particulates | ≥10 μm: 13 per unit ≥25 μm: 0 per unit | ≥10 μm: 5 per unit ≥25 μm: 0 per unit | ≥10 μm: 4 per unit ≥25 μm: 0 per unit |
| Microbial Enumeration/ Specified Microorganisms | | | |
| Total Aerobic Microbial Count | 0 CFU/mL | 0 CFU/mL | 0 CFU/mL |
| Total Yeasts and Mold Count | 0 CFU/mL | 0 CFU/mL | 0 CFU/mL |
| *Staphylococcus aureus* | Absence | Absence | Absence |
| *Pseudomonas aeruginosa* | Absence | Absence | Absence |
| *Escherichia coli* | Absence | Absence | Absence |
| Bile-Tolerant Gram-Negative Bacteria | <10 CFU/mL | <10 CFU/mL | <10 CFU/mL |

The degradation products of formulation A-2 were tested. The procedure used for this test is described in the above Methods of Preparation and Characterization. Table 2e summarizes data for this formulation. The names of the specified Impurities (i.e., Impurities A, C, E, and F) are named in accordance with the European Pharmacopeia. The study also included an analysis of an additional degradation product named below as Degradation Product 1, and an additional impurity analysis (Additional 1).

TABLE 2e

| Exemplary degradation properties of formulation A-2 | | | |
|---|---|---|---|
| Test | Batch 1 | Batch 2 | Batch 3 |
| Degradation Products Specified Identified Impurities | | | |
| Impurity A | Not Detected | <0.05% | <0.05% |
| Impurity C | Not Detected | Not Detected | Not Detected |
| Impurity E | Not Detected | Not Detected | <0.05% |
| Impurity F | Not Detected | Not Detected | Not Detected |
| Naloxone N-oxide | Not Detected | Not Detected | Not Detected |
| Degradation Product 1 | Not Detected | 0.08% | 0.08% |
| Additional Impurities | | | |
| Additional 1 | 0.08% | <0.05% | <0.05% |
| Total Degradation Products | 0.08% | 0.08% | 0.08% |

Example 3: Exemplary Formulation A-3

The below exemplary formulation was prepared, autoclaved, and characterized based on the procedures described in the above Methods of Preparation and Characterization. The composition makeup of the formulation is described in Table 3a, exemplary properties are described in Table 3b, exemplary spray pattern properties are described in Tables 3c and 3d, and exemplary degradation properties are described in Table 3e.

TABLE 3a

| Exemplary formulation A-3 | | |
|---|---|---|
| Component | Grade | Composition % w/w |
| Naloxone HCl Dihydrate (corresponding to naloxone HCl) | USP | 10.62 (9.66) |
| Glycerin | USP | 1.35 |
| Trisodium citrate Dihydrate | USP | 0.014 |
| Citric Acid, Anhydrous | USP | 0.008 |
| Hydrochloric Acid | NF | AR |
| Sodium Hydroxide | NF | AR |
| Purified Water | USP | QS |
| Total: | | 100.00 |

Formulation A-3 was tested for product appearance, packaging, pH, osmolality and assay. Formulation A-3 was also tested for microbial enumeration/specified microorganisms. The procedure used for the tests are described in the above Methods of Preparation and Characterization. Table 3b summarizes data for this formulation.

TABLE 3b

| Exemplary properties of formulation A-3 | |
|---|---|
| Test | Result |
| Aspect | |
| Product Appearance | A clear, light yellow solution. |
| Packaging | Conforms |
| pH | 4.5 |
| Osmolality | 538 mOsm |
| Assay | 101.1% |
| Microbial Enumeration/ Specified Microorganisms | |
| Total Aerobic Microbial Count | 0 CFU/mL |
| Total Yeasts and Molds Count | 0 CFU/mL |

A spray of formulation A-3 was tested for SCU and pump delivery. The procedure used for the tests are described in the above the above Methods of Preparation and Characterization. Table 3c summarizes data for this formulation.

TABLE 3c

| Exemplary spray pattern properties of formulation A-3 | | |
|---|---|---|
| Test | Result | |
| Spray Content Uniformity (SCU) | Mean | 100% |
| Pump Delivery | Mean | 100% |

A spray of formulation A-3 was tested for droplet size distribution and spray pattern. The procedure used for the tests are described in the above Methods of Preparation and Characterization. Table 3d summarizes data for this formulation.

TABLE 3d

| Exemplary spray pattern properties of formulation A-3 | |
|---|---|
| Test | Result |
| Droplet Size Distribution | |
| $D_{10}$ | 12.13 μm |
| $D_{50}$ | 27.10 μm |
| $D_{90}$ | 60.66 μm |
| % V < 10 μm | 6% |
| Span | 1.79 |
| Spray Pattern | |
| Shape | Conforms |
| Density | Conforms |
| $D_{max}$ | 41 mm |
| Ovality | 1.2 |

A spray of formulation A-3 was tested for degradation properties. The procedure used for the tests are described in the above Methods of Preparation and Characterization. Table 3e summarizes data for this formulation. The names of the specified Impurities (i.e., Impurities A, C, D, and E) are named in accordance with the European Pharmacopeia. The study also included an additional impurity analysis (Additional 1).

TABLE 3e

| Exemplary degradation properties of formulation A-3 | | |
|---|---|---|
| Test | Result | |
| Net Content | Mean | 129.80 mg |
| Related Compounds | | |
| Specified Identified Impurities | | |
| Impurity A | Not Detected | |
| Impurity B | Not Detected | |
| Impurity C | Not Detected | |
| Impurity D | Not Detected | |
| Impurity E | 0.05% | |
| Naloxone-N-oxide | Not Detected | |
| Additional Impurities | | |
| Additional 1 | 0.09% | |
| Total Impurities | 0.09% | |

Example 4: Exemplary Formulation A-4

The below exemplary formulation was prepared based on the procedures described in the above Methods of Preparation and Characterization. The composition makeup of the formulation is described in Table 4a.

TABLE 4a

| Exemplary formulation A-4 | | |
|---|---|---|
| Ingredient | Autoclaved Quantity (g) | Alternate Preservative Quantity (g) |
| Naloxone HCl Dihydrate | 10.99 | 10.99 |
| Benzyl Alcohol | N/A | 0.9 |
| Citric Acid, Anhydrous | 0.00857 | 0.00857 |
| Trisodium Citrate Dihydrate | 0.0148 | 0.0148 |
| Glycerin | 1.4 | 1.4 |
| NaOH/HCl | As required | As required |
| Purified Water | QS to 100 mL | QS to 100 mL |

Example 5. Exemplary Formulations

Additional exemplary formulations and their ingredient amounts by column are provided in FIGS. 1-9, which were prepared using the methods described above.

Example 6. Stability Studies of Naloxone HCl Formulation

Stability studies of the Naloxone HCl formulation (unit dose) are described. Tables 5a and 5b describe these studies for Naloxone HCl sample prepared according to the process of Example 2 at the indicated time points, including the conditions (temperature) applied and determination of the amount of Impurity (Impurity A, C, E or F) in the samples. The studies show that the Naloxone HCl formulation is surprisingly highly stable.

TABLE 5a

| Studies of Naloxone HCl formulation prepared according to the process of Example 2 | | | | | |
|---|---|---|---|---|---|
| Time Point | Initial | 1 Month | 3 Months | 6 Months | 9 Months |
| Condition Degradation Products Specified Identified Impurities | 25° C. | 25° C. | 25° C. | 25° C. | 25° C. |
| Impurity A | Not Detected | < 0.05% | Not Detected | Not Detected | Not Detected |
| Impurity C | Not Detected | Not Detected | Not Detected | Not Detected | Not Detected |
| Impurity E | Not Detected | < 0.05% | Not Detected | Not Detected | Not Detected |
| Impurity F | Not Detected | Not Detected | Not Detected | Not Detected | Not Detected |
| Naloxone-N-oxide | Not Detected | Not Detected | Not Detected | Not Detected | Not Detected |
| Degradation Product 1 | 0.08% | 0.14% | 0.18% | 0.34% | 0.40% |
| Total Degradation Products | 0.08% | 0.14% | 0.23% | 0.34% | 0.50% |

TABLE 5b

| Studies of Naloxone HCl formulation prepared according to the process of Example 2 | | | | | |
|---|---|---|---|---|---|
| Time Point | Initial | 1 Month | 3 Months | 6 Months | 9 Months |
| Condition Degradation Products Specified Identified Impurities | 40° C. | 40° C. | 40° C. | 40° C. | 40° C. |
| Impurity A | Not Detected | <0.05% | 0.05% | Not Detected | 0.11% |
| Impurity C | Not Detected | Not Detected | Not Detected | Not Detected | Not Detected |
| Impurity E | Not Detected | <0.05% | Not Detected | Not Detected | Not Detected |
| Impurity F | Not Detected | Not Detected | Not Detected | Not Detected | Not Detected |
| Naloxone-N-oxide | Not Detected | Not Detected | Not Detected | 0.17% | 0.26% |
| Degradation Product 1 | 0.08% | 0.29% | 0.38% | 0.52% | 0.53% |
| Total Degradation Products | 0.08% | 0.43% | 0.68 | 0.89% | 1.2% |

Example 7. Pharmacokinetic Studies of a Spray of Naloxone HCl Formulation

Studies comparing pharmacokinetics of one nasal spray of a 10 mg total dose (0.1 mL of 91 mg/mL Naloxone HCl solution) as prepared in Example 2 and a single dose of 0.4 mg Naloxone HCl intramuscular injection and a single dose of 2 mg Naloxone HCl intravenous injection were conducted in 30 healthy adult subjects. Subjects receiving the nasal spray via intranasal administration were instructed not to breathe through the nose during the administration, and the subjects remained fully supine for approximately one hour post-dose. For the intramuscular administration, the Naloxone was administered as a single injection in the gluteus maximus muscle. For the intravenous administration, the Naloxone was administered as an intravenous bolus. The results of the study are shown in Table 6, which demonstrates an unexpected enhanced pharmacokinetic profile for the nasal spray of Naloxone HCl formulation.

TABLE 6

| Pharmacokinetic data. | | | |
|---|---|---|---|
| Parameter (units) | Nasal Spray 10 mg (n = 29) | Intramuscular Injection 0.4 mg (n = 30) | Intravenous Injection 2 mg (n = 23) |
| $t_{max}$ (h) † | 0.75 (0.25, 1.03) | 0.50 (0.17, 2.00) | 0.08 (0.02, 0.18) |
| $C_{max}$ (ng/ml) | 9.11 (35.45) | 0.74 (36.63) | 18.41 (46.08) |
| $AUC_{(0-t)}$ (h · ng/mL) | 19.19 (24.81) | 1.92 (19.75) | 12.18 (24.30) |
| $AUC_{(0-\infty)}$ (h · ng/mL) | 19.52 (24.78) | 1.98 (19.18) | 12.25 (24.22) |
| $t_{1/2}$ (h) | 1.33 (16.09) | 1.22 (18.48) | 1.18 (11.59) |
| Dose normalized absolute BA vs. IV†† | 0.34 (30.53) | 0.84 (29.06) | — |

† tmax reported as median (minimum, maximum)

†† N = 22 and N = 23, respectively for Nasal Spray 10 mg and Naloxone HCl 0.4 mg Intramuscular Injection for Dose normalized absolute BA vs. IV The plasma concentrations of naloxone were measured by collecting blood samples at pre-dose (up to 60 minutes before dosing; 0-hour) and at intervals over 8 hours dosing in each study period. As shown in Table 6, the dose normalized absolute bioavailability of the nasal spray with 10 mg Naloxone HCl (one dose) and 0.4 mg of Naloxone HCl intramuscular injection compared to 2 mg of naloxone HCl intravenous injection was 34% and 84%, respectively.

As described in Table 6, following a single intranasal administration of the nasal spray (10 mg dose of Naloxone hydrochloride), the mean plasma half-life of Naloxone in healthy adults was approximately 1.33 hours (16.09% CV) hours. This was longer than that observed after administrations of a 0.4 mg Naloxone hydrochloride intramuscular injection and a 2 mg Naloxone hydrochloride intravenous injection, where the half-life was 1.22 hours (18.48% CV) and 1.18 hours (11.59% CV), respectively. In a neonatal study of Naloxone hydrochloride injection, the mean (±SD) plasma half-life was observed to be 3.1 (±0.5) hours.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description. Those of ordinary skill in the art will appreciate that various changes and modifications to this description may be made without departing from the spirit or scope of the present invention, as defined in the following claims.

What is claimed is:

1. A unit dose of an aqueous pharmaceutical solution housed in a device configured for intranasal administration to a patient, wherein the aqueous pharmaceutical solution consists of:

(i) naloxone hydrochloride in an amount of about 9% by weight based on the total weight of the aqueous pharmaceutical solution;

(ii) glycerin in an amount of about 1.4% by weight based on the total weight of the aqueous pharmaceutical solution;

(iii) a citrate buffer system adjusted by hydrochloric acid and/or sodium hydroxide; and (iv) United States Pharmacopeia (USP)-grade Purified Water;

wherein the pH of the aqueous pharmaceutical solution is from about 3.5 to about 4.7; and wherein the hydrochloric acid and the sodium hydroxide may each be independently present in the aqueous pharmaceutical solution, as required, to achieve the pH from about 3.5 to about 4.7;

wherein the osmolality of the aqueous pharmaceutical solution is about 560 mOsm/kg; and wherein the device is configured to deliver the unit dose to the patient by a single actuation.

2. The unit dose of claim 1, wherein the pH of the solution is about 4.3.

3. The unit dose of claim 1, wherein the citrate buffer is in an amount of about 0.2% to about 0.4% by weight based on the total weight of the aqueous pharmaceutical solution.

4. The unit dose of claim 1, wherein the unit dose maintains at least 98 wt % of the naloxone hydrochloride upon storage under the conditions of 40° C. for at least 1 month.

5. The unit dose of claim 1, wherein the unit dose maintains at least 98 wt % of the naloxone hydrochloride upon storage under the conditions of 40° C. for at least 3 months.

6. The unit dose of claim 1, wherein the unit dose maintains at least 98 wt % of the naloxone hydrochloride upon storage under the conditions of 40° C. for at least 6 months.

7. The unit dose of claim 1, wherein the unit dose maintains at least 98 wt % of the naloxone hydrochloride upon storage under the conditions of 40° C. for at least 9 months.

* * * * *